(12) United States Patent
Barrett et al.

(10) Patent No.: US 6,251,943 B1
(45) Date of Patent: Jun. 26, 2001

(54) METHOD OF TREATING OR PREVENTING SEPTIC SHOCK BY ADMINISTERING A MEK INHIBITOR

(75) Inventors: Stephen Douglas Barrett, Livonia; Alexander James Bridges; Donna Reynolds Cody, both of Saline, all of MI (US); Annette Marian Doherty, Anthony (FR); David Thomas Dudley; Alan Robert Saltiel, both of Ann Arbor, MI (US); Mel Conrad Schroeder, Dexter, MI (US); Haile Tecle, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/355,680

(22) PCT Filed: Dec. 17, 1997

(86) PCT No.: PCT/US97/23389

§ 371 Date: Aug. 2, 1999

§ 102(e) Date: Aug. 2, 1999

(87) PCT Pub. No.: WO98/37881

PCT Pub. Date: Sep. 3, 1998

Related U.S. Application Data

(60) Provisional application No. 60/039,270, filed on Feb. 28, 1997, and provisional application No. 60/056,157, filed on Aug. 19, 1997.

(51) Int. Cl.$^7$ ............... A61K 31/195; A61K 31/165; A61K 31/135

(52) U.S. Cl. ............... 514/564; 514/620; 514/657; 514/658; 514/921

(58) Field of Search ................... 514/564, 620, 514/921, 657, 658

(56) References Cited

FOREIGN PATENT DOCUMENTS 9622985    8/1996  (WO).
9636642    11/1996 (WO).
9722704    6/1997  (WO).

OTHER PUBLICATIONS

J.T. Van Der Bruggen et al; "Modulation of Endotoxin–Induced Tumor Necrosis Factor alpha Release by Human Monocytes"; Mar. 1997; European Journal of Clinical Investigation; vol. 27, No. S1, p. A19.

T.D. Geppert et al; "Lipoplysaccharide Signals Activation of Tumor Necrosis Factor Biosnthesis Through the RAS/RAF–1/MEK/MPAK Pathway"; 1994, Molecular Medicine, vol. 1, No. 1, pp. 93–103.

D.T. Dudley et al; "A Synthetic Inhibitor of the Mitogen–Activated Protein Kinase Cascade"; 1995; Proc. Natl. Acad. Sci.; vol. 92, No. 17, pp. 7686–7689.

H. Bekemeier et al; "Structure–Activity Relationship in Nonsteroidal Anti Inflammatory Agents, Including Qsar in Fenamate Derivatives"; 1982; Agents Actions Suppl.; pp. 17–34.

P. Ramanujam et al; "Antifungal Activity of Some N–Substituted Anthranilic Acid Derivatives"; 1974; Planta Medica; vol. 25, No. 1, pp. 43–46.

N.H. Berner et al; "Substituted N–Phenylanthranilic Acid Hydrazides as Potential Antimalarial and Antimicrobial Agents"; 1970; Journal of Medicinal Chemistry; vol. 13, No. 3, pp. 552–554.

A.N. Gaidukevich et al; "Synthesis and Biological Activity of N–Phenylanthranilic Acid" Sep. 16, 1985; Chemical Abstracts; vol. 103, No. 11 (abstract).

T.I. Shul'ga et al; "Synthesis and Physiochemical and Biological Properties of Diphenylamine–2–Carboxylic Acid Derivatives"; Oct. 24, 1988; Chemical Abstracts; vol. 109, No. 17 (abstract).

I.S. Shul'ga et al; "Synthesis of 6–Nitrodiphenylamine–2–Carboxylic Acid Derivatives their Physiocochemical and Antimicrobial Properties"; Nov. 6, 1972; Chemical Abstracts; vol. 77, No. 19 (abstract).

*Primary Examiner*—Frederick Krass
*Assistant Examiner*—Donna Jagoe
(74) *Attorney, Agent, or Firm*—Charles W. Ashbrook

(57) ABSTRACT

The present invention provides a method for treating or preventing septic shock. Specifically, the present invention provides a method of treating or preventing septic shock by administering to a patient a MEK inhibitor.

9 Claims, No Drawings

METHOD OF TREATING OR PREVENTING SEPTIC SHOCK BY ADMINISTERING A MEK INHIBITOR

This application is a 371 of PCT WO/98/37881, filed Dec. 17, 1997 and Provisional application No. 60/039,270, filed Feb. 28, 1997, which claims benefit to U.S. Provisional application No. 60/056,157, filed Aug. 19, 1997.

FIELD OF THE INVENTION

The present invention relates to a method of treating or preventing septic shock in a patient by administering to the patient a compound that is a MEK inhibitor.

BACKGROUND OF THE INVENTION

Septic shock is a serious medical condition that is caused by invasion of the circulatory system by bacteria. Septic shock is characterized by acute circulatory failure, usually with hypotension, followed by multiple organ failure and acute renal failure. The mortality rate of patients having septic shock is in the range of 25% to 90%. It is estimated that up to 500,000 people a year in both the United States and Europe develop septic shock.

The human immune system has many dedicated receptor systems that detect common pathogens, especially bacteria, and these receptor systems are distinct from the specific antibody and T-cell receptor systems, because they are permanently present, and are not tailored to meet a particular threat. Many of the dedicated receptor systems recognize the structural components of bacteria, such as lipopolysaccharide (LPS) lipoteichoic acid and peptidoglycan, and lead to activation of the immune system when these receptors bind structural components of bacteria.

LPS, a major component of the outer cell membrane of gram-negative bacteria, appears to be a major factor in the progression of a bacterial infection to septic shock. The principal mechanism for recognition by the human immune system of LPS is by binding of the CD14 receptor on macrophages to LPS. This binding requires LPS Binding Protein (LBP), an inducible protein made in the liver. Once macrophages have bound and recognized LPS, the macrophages produce massive amounts of inflammatory cytokines, especially tumor necrosis factor-α(TNF α), Interleukin 1 β(IL- 1β), and Interleukin 6 (IL-6).

Three of the transcription factors important in inducing LBP production in the liver are AP-1, C/EBP and STAT-3. All of these can be stimulated through the IL-6 signaling pathway, which is produced locally in the liver by Kuppfer cells. IL-6 stimulates the MAP kinases Mitogen-Activated Protein Kinases, also known as Extracellular Signal-Regulated Kinase or ERK, of which there are two isoforms (also called ERK1 and ERK2) through MEK, (the name given to MAP-kinase, namely Mitogen-Activated Protein Kinase Kinase), and these MAP kinases can activate the three transcription factors mentioned above by phosphorylation. Thus, an inhibitor of MEK can decrease the stimulation of LBP gene transcription, and attenuate the strength of the macrophage response to LPS.

In macrophages, LPS signaling appears to activate all three of the known MAP kinase pathways, including the MEK/ERK cascade, and LPS stimulation of macrophages leads to rapid and major activation of ERKs. ERK is believed to be one of the kinases that phosphorylates IκB, a prerequisite for the liberation of the transcription factor NF κB. NF κB, once liberated, enters the nucleus, and is probably the single most important transcriptional activator for production of TNF α. Thus, an inhibitor of MEK or ERK activity could also decrease the stimulation of TNF-α gene transcription, leading to a greatly decreased physiological response to LPS.

In cells that contain the TNF receptor, activation of that receptor leads to turning on of many pathways that lead to toxicity in the target cell, and which culminate in apoptosis (regulated self-destruction of the cell). Multiple organ failure is more likely caused by TNF-α induced toxicity than by any other single cause. Neutral sphingomyelinase has been shown to be activated by the TNF receptor, and this, in turn, activates ceramide-activated protein kinase, which then activates the MEK/MAP kinase pathway in the target cells, probably adding to the overall toxic effects of TNF.

Thus, the MEK/MAP kinase pathway is important in septic shock, and is involved at several vital points in the progression of septic shock.

SUMMARY OF THE INVENTION

The present invention provides a method of treating or preventing septic shock, the method comprising administering to a patient having septic shock or at risk of having septic shock a therapeutically acceptable amount of a compound that is a MEK inhibitor.

In a preferred embodiment of the invention the MEK inhibitor is 2-(2-amino-3-methoxyphenyl)4-oxo-4H-[1] benzopyran.

In another preferred embodiment of the invention, the patient has septic shock.

In another preferred embodiment of the invention, the patient is at risk of having septic shock.

In a more preferred embodiment the invention provides a method of treating or preventing septic shock, the method comprising administering to a patient having septic shock or at risk of having septic shock a therapeutically acceptable amount of 2-(2-amino-3-methoxyphenyl)-4-oxo-4H-[1] benzopyran.

In a preferred embodiment of the invention, the MEK inhibitor is a compound of Formula I

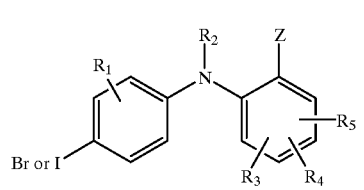

I wherein:
$R_1$ is hydrogen, hydroxy, $C_1$–$C_8$ alkyl, $C_1$–$C_8$ alkoxy, halo, trifluoromethyl, or CN;
$R_2$ is hydrogen;
$R_3$, $R_4$, and $R_5$ independently are hydrogen, hydroxy, halo, trifluoromethyl, $C_1$–$C_8$ alkyl, $C_1$–$C_8$ alkoxy, nitro, CN, or —(O or NH)$_m$—(CH$_2$)$_n$—R$_9$, where R$_9$ is hydrogen, hydroxy, COOH, or $NR_{10}R_{11}$;
n is 0–4;
m is 0 or 1;
$R_{10}$ and $R_{11}$ independently are hydrogen or $C_1$–$C_8$ alkyl, or taken together with the nitrogen to which they are attached can complete a 3–10 member cyclic ring optionally containing 1, 2, or 3 additional heteroatoms selected from O, S, NH, or N—$C_1$–$C_8$ alkyl;

Z is COOR$_7$, tetrazolyl, CONR$_6$R$_7$, CONHNR$_{10}$R$_{11}$, or CH$_2$OR$_7$;

R$_6$ and R$_7$ independently are hydrogen, C$_1$–C$_8$ alkyl, C$_2$–C$_8$ alkenyl, C$_2$–C$_8$ alkynyl,

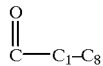

alkyl, aryl, heteroaryl, C$_3$–C$_{10}$ cycloalkyl, or C$_3$–C$_{10}$ (cycloalkyl optionally containing one, two, or three heteroatoms selected from O, S, NH, or N alkyl); or R$_6$ and R$_7$ together with the nitrogen to which they are attached complete a 3–10 member cyclic ring optionally containing 1, 2, or 3 additional heteroatoms selected from O, S, NH, or N alkyl;

and wherein any of the foregoing alkyl, alkenyl, and alkynyl groups can be unsubstituted or substituted by halo, hydroxy, alkoxy, amino, alkylamino, dialkylamino, cycloalkyl, aryl, aryloxy, heteroaryl, or heteroaryloxy, and the pharmaceutically acceptable salts, esters, amides, or prodrugs thereof.

In a more preferred embodiment, the MEK inhibitor is

[4-Chloro-2-(1H-tetrazol-5-yl)-(4iodo-2-methyl-phenyl)-amine;
(4-iodo-2-methyl-phenyl)-[2-(1H-tetrazol-5-yl)-phenyl]amine;
[4-nitro-2-(1H-tetrazol-5-yl)-(4-iodo-2-methyl-phenyl)-amine;
4-Fluoro-2-(4-iodo-2-methylphenylamino)benzoic acid;
3,4,5-Trifluoro-2-(4-iodo-2-methyl-phenylamino)-benzoic acid;
3,4-Difluoro-2-(4-iodo-2-methyl-phenylamino)-benzoic acid;
5-Bromo-3,4-difluoro-2-(4-iodo-2-methyl-phenylamino)-benzoic acid;
5-Chloro-2-(4-iodo-2-methyl-phenylamino)-benzoic acid;
Sodium 5-Chloro-2-(4-iodo-2-methyl-phenylamino)-benzoate;
5-Bromo-2-(4-iodo-2-methyl-phenylamino)-benzoic acid;
2-(4-Iodo-2-methyl-phenylamino)-5-nitro-benzoic acid;
4-Chloro-2-(4-iodo-2-methyl -phenylamino)-benzoic acid;
2-(4-Iodo-2-methyl-phenylamino)-benzoic acid;
5-Fluoro-2-(4-iodo-2-methyl-phenylamino)-benzoic acid;
5-Iodo-2-(4-iodo-2-methyl-phenylamino)-benzoic acid;
2,3,5-Trifluoro-4-(4-iodo-2-methyl-phenylamino)-benzoic acid;
2-(4-Iodo-phenylamino)-5-methoxy-benzoic acid;
5-Methyl-2-4-iodo-2-methyl-phenylamino)-benzoic acid;
2-(4-Iodo-2-methyl-phenylamino)-4-nitro-benzoic acid;
2-(4-Bromo-2-methyl-phenylamino)4-fluoro-benzoic acid;
2-(2-Bromo-4-iodo-phenylamino)-5-nitro-benzoic acid;
2-(4-Bromo-2-methyl-phenylamino)-3,4-difluoro-benzoic acid;
5-Chloro-N-(2-hydroxyethyl)-2-(4-iodo-2-methyl-phenylamino)-benzamide;
4-Fluoro-2-(4-iodo-2-methyl-phenylamino)-benzamide;
4-Fluoro-2-(4-iodo-2-methyl-phenylamino)-N-methyl-benzamide;
N-Ethyl4-fluoro-2-(4-iodo-2-methyl-phenylamino)-benzamide;
4-Fluoro-2-(4-iodo-2-methyl-phenylamino)-N,N-dimethyl-benzamide;
4-Fluoro-2-(4-iodo-2-methyl-phenylamino)-N-(1H-tetrazol-5-yl)-benzamide;
5-Bromo-2-(4-iodo-2-methyl-phenylamino)-benzamide;
5-Chloro-2-(4-iodo-2-methyl-phenylamino)-N,N-dimethyl-benzamide;
[5-Chloro-2-(4-iodo-2-methyl-phenylamino)-benzoylamino]-acetic acid;
4-Fluoro-2-(4-iodo-2-methyl-phenylamino)-N-propyl-benzamide;
5-Bromo-N-(2-hydroxy-ethyl)-2(4-iodo-2-methyl-phenylamino)-benzamide;
N,N-Diethyl-4-fluoro-2-(4-iodo-2-methyl-phenylamino)-benzamide;
4-Fluoro-N-{3-[4-(2-hydroxy-ethyl)-piperazin-1-yl]-propyl}-2-(4-iodo-2-methyl-phenylamino)-benzamide;
N,N-Diethyl-2-(4-iodo-2-methyl-phenylamino)-5-nitro-benzamide;
N-Butyl-4-fluoro-2-(4-iodo-2-methyl-phenylamino)-benzamide;
5-Chloro-N,N-diethyl-2-(4-iodo-2-methyl-phenylamino)-benzamide;
5-Bromo-2-(4-iodo-2-methyl-phenylamino)-N,N-dimethyl-benzamide;
5-Bromo-3,4-difluoro-N-(2-hydroxy-ethyl)2-(4-iodo-2-methyl-phenylamino)-benzamide;
N-(2,3-Dihydroxy-propyl)-3,4-difluoro-2-(4-iodo-2-methyl-phenylamino)-benzamide;
5-Bromo-3,4-difluoro-2-(4-iodo-2-methyl-phenylamino)-N-(2-piperidin-1-yl-ethyl)-benzamide;
3,4-Difluoro-N-(2-hydroxy-ethyl-2-(4-iodo-2-methyl-phenylamino)-benzamide;
N-(2,3-Dihydroxy-propyl)-4-fluoro-2-(4-iodo-2-methyl-phenylamino)-benzanide;
3,4-Difluoro-N-(3-hydroxy-propyl)-2-(4-iodo-2-methyl-phenylamino)-benzamide;
5-Bromo-3,4-difluoro-2-(4-iodo-2-methyl-phenylamino)-N-(2-pyrrolidin-1-yl-ethyl)-benzamide;
5-Bromo-3,4-difluoro-2-(4-iodo-2-methyl-phenylamino)-N-(2-pyridin4yl-ethyl)-benzamide;
4-Fluoro-N-(2-hydroxy-ethyl)-2-(4-iodo-2-methyl-phenylamino)-benzamide;
5-Bromo-N-(3-dimethylamino-propyl)-3,4-difluoro-2-(4-iodo-2-methyl-phenylamino)-benzamide;
5-Bromo-3,4-difluoro-2-(4iodo-2-methyl-phenylamino)-N-(2-morpholin-4-yl-ethyl)-benzamide;
3,4-Difluoro-2-(4-iodo-2-methyl-phenylamino)-N-(2-morpholin-4-yl-ethyl)-benzamide;
3,4-Difluoro-2-(4-iodo-2-methyl-phenylamino)-N-(2-pyrrolidin-1-yl-ethyl)-benzamide;
3,4-Difluoro-2-(4-iodo-2-methyl-phenylamino)-N-(2-pyridin-4-yl-ethyl)-benzamide;
N-(3-Dimethylamino-propyl)-3,4-difluoro-2-(4-iodo-2-methyl-phenylamino)-benzamide;
N-Benzyl-4-fluoro-2-(4-iodo-2-methyl-phenylamino)-benzamide;

2-(4-Bromo-2-methyl-phenylamino)-3,4-difluoro-N-(2-hydroxy-ethyl)benzamide;

4-Fluoro-2-(4-iodo-2-methyl-phenylamino)-N-(2-morpholin-4-yl-ethyl)-benzamide;

4-Fluoro-2-(4-iodo-2-methyl-phenylamino)-N-(3-piperidin-1-yl-propyl)-benzamide;

3,4-Difluoro-2-(4-iodo-2-methyl-phenylamino)-N-(3-piperidin-1-yl-propyl)benzamide;

4-Fluoro-2-(4-iodo-2-methyl-phenylamino)-N-(2-thiophen-2-yl-ethyl)-benzamide;

4-Fluoro-2-(4-iodo-2-methyl-phenylamino)-N-(2-pyrrolidin-1-yl-ethyl)-benzamide;

2-(4-Bromo-2-methyl-phenylamino)3,4-difluoro-N-(2-morpholin-4-yl-ethyl)-benzamide;

5-Bromo-3,4-difluoro-2-(4-iodo-2-methyl-phenylamino)-N-pyridin-4ylmethyl-benzamide;

3,4-Difluoro-2-(4-iodo-2-methyl-phenyl amino)-N-pyridin-4-ylmethyl-benzamide;

2-(4-Bromo-2-methyl-phenylamino)N-(3-dimethylamino-propyl)-3,4-difluoro-benzamide;

4-Fluoro-2-(4-iodo-2-methyl-phenylamino)N-pyridin-4-ylmethyl-benzamide;

4-Fluoro-2-(4-iodo-2-methyl-phenylarnino)-N-(2-pyridin-4-yl-ethyl)-benzamide;

2-(4-Bromo-2-methyl-phenylamino)-3,4-difluoro-N-(2-pyridin-4-yl-ethyl)-benzamide;

2-(4-Bromo-2-methyl-phenylamino)-3,4-difluoro-N-(3-hydroxy-propyl)-benzamide;

2-(4-Bromo-2-methyl-phenylamino)-3,4-difluoro-N-(2-pyrrolidin-1-yl-ethyl)-benzamide;

4-Fluoro-2-(4-iodo-2-methyl-phenylamino)-N-phenethyl-benzamide;

2-(4-Bromo-2-methyl-phenylamino)-3,4-difluoro-N-(2-thiophen-2-yl-ethyl)-benzamide;

2-(4-Bromo-2-methyl-phenylamino)-3,4-difluoro-N-pyridin-4-ylmethyl-benzamide;

2-(4-Bromo-2-methyl-phenylamino)3,4-difluoro-N-phenethyl-benzamide;

2-(4-Bromo-2-methyl-phenylamino)-3,4-difluoro-N-(2-piperidin-1-yl-ethyl)-benzamide;

5-Chloro-N-{3-[4-(2-hydroxy-ethyl)-piperazin-1-yl]-propyl}-2-(4-iodo-2-methyl-phenylamino)-benzamide;

5-Fluoro-N-{3-[4-(2-hydroxy-ethyl)-piperazin-1-yl]-propyl}-2-(4-iodo-2-methyl-phenylamino)-benzamide;

2-(4-Iodo-2-methyl-phenylamino)-5-nitro-N-pyridin4-yl methyl-benzamide;

5-Bromo-N- {3-[4-(2-hydroxy-ethyl)-piperazin-1-yl]-propyl}-2-(4-iodo-2-methyl-phenylamino)-benzamide;

5-Chloro-N-(2-diethylamino-ethyl)-2-(4-iodo-2-methyl-phenylamino)-benzamide;

5-Chloro-2-(4-iodo-2-methyl-phenylamino)-N-(2-piperidin-1-yl-ethyl)-benzamide;

(3-Hydroxy-pyrrolidin-1-yl)-[2-(4iodo-2-methyl-phenylamino)-5-nitro-phenyl];

5-Chloro-2-(4-iodo-2-methyl-phenylamino)-N-(2-pyrrolidin-1-yl-ethyl)benzamide;

5-Bromo-N-(2-diethylamino-ethyl)-2-(4-iodo-2-methyl-phenylamino)-benzamide;

N-{2-[Bis-(2-hydroxy-ethyl)-amino]-ethyl}-5-chloro-2-(4-iodo-2-methyl-phenylamino)-benzamide;

N-{2-[Bis-(2-hydroxy-ethyl)-amino]-ethyl}-5-bromo-2-(4-iodo-2-methyl-phenylamino)-benzamide;

N-{3-[4-(2-Hydroxy-ethyl)-piperazin-1-yl]-propyl}-2-(4-iodo-2-methyl-phenylamino)-benzamide;

5-Fluoro-2-(4-iodo-2-inethyl-phenylamino)-N-pyridin-4-yl-methyl-benzamide;

5-Bromo-2-(4-iodo-2-ethyl-phenylamino)-N-(2-pyrrolidin-1-yl-ethyl)-benzamide;

5-Bromo-2-(4-iodo-2-methyl-phenylamino)-N-2-piperidin-1-yl-ethyl)-benzamide;

5-Fluoro-2-(4-iodo-2-methyl-phenylamino)-N-(2-pyrrolidin-1-yl-ethyl)-benzamide;

5-Chloro-N-(3-dimethylamino-propyl)-2-4-iodo-2-methyl-phenylamino)-benzamide;

N-{2-[Bis-(2-hydroxy-ethyl)-amino]-ethyl}-5-fluoro-2-(4-iodo-2-methyl-phenylamino)-benzamide;

5-Chloro-N-3-hydroxy-propyl)-2-(4-iodo-2-methyl-phenylamino)-benzamide;

5-Chloro-N-(3-diethylamino-2-hydroxy-propyl)-2-(4-iodo-2-methyl-phenylamino)-benzamide;

5-Fluoro-2-(4iodo-2-methyl-phenylamino)-N-(2-piperidin-1-yl-ethyl)-benzamide;

5-Bromo-N-(3-hydroxy-propyl)-2-(4-iodo-2-methyl-phenylamino)-benzamide;

5-Bromo-2-(4iodo-2-methyl-phenylamino)-N-(3-piperidin-1-yl-propyl)-benzamide;

N-{2-[Bis-(2-hydroxy-ethyl)-amino]-ethyl}-2-(4-iodo-2-methyl-phenylamino)-5-nitro-benzamide;

5-Chloro-2-(4-iodo-2-methyl-phenylamino)-N-(2-morpholin4-yl-ethyl)-benzamide;

5-Chloro-N-(3-diethylamino-propyl)-2-(4-iodo-2-methyl-phenylamino)-benzamide;

5-Chloro-N-(2-diisopropylamino-thyl)-2-(4-iodo-2-methyl-phenylamino)-benzamide;

5-Chloro-2-(4-iodo-2-methyl-phenylamino)-N-(3-piperidin-1-yl-propyl)-benzamide;

2-(4-Iodo-2-methyl-phenylamino)-5-nitro-N-2-piperidin-1-yl-ethyl)-benzamide;

5-Bromo-2-(4-iodo-2-methyl-phenylamino)-N-(2-piperazin-1-yl-ethyl)-benzanide;

N-(2-Diethylamino-ethyl)5-fluoro-2-4-iodo-2-methyl-phenylamino)-benzamide;

5-Bromo-N-(3-dimethylamino-propyl)2-(4-iodo-2-methyl-phenylamino)-benzaminde;

N-(3-Hydroxy-propyl)-2-(4-iodo-2-methyl-phenylamino)-5-nitro-benzamide;

5-Fluoro-N-(3-hydroxy-propyl)-2-(4-iodo-2-methyl-phenylamino)-benzamide;

N-(3-Diethylamino-propyl)-5-fluoro-2-(4-iodo-2-methyl-phenylamino)-benzamide;

N-(3-Diethylamino-propyl)2-(4-iodo-2-methyl-phenylamino)-5-nitro-benzamide;

5-Bromo-2(4-iodo-2-methyl-phenylamino)-N-(2-morpholin4-yl-ethyl)-benzamide;

2-(4Iodo-2-methyl-phenylamino)-5-nitro-N-(3-piperidin-1-yl-propyl)-benzamide;

[5-Fluoro-2-(4-iodo-2-methyl-phenylamino)-phenyl]-(3-hydroxy-pyrrolidin-1-yl);

5-Bromo-N-(2-diisopropylamino-ethyl)-2-(4-iodo-2-methyl-phenylamino)-benzamide;

5-Fluoro-2-(4-iodo-2-methyl-phenylamino)-N-(2-morpholin-4-yl-ethyl)-benzamide;

5-Fluoro-2-(4-iodo-2-methyl-phenylamino)-N-(3-piperidin-1-yl-propyl)-benzamide;

[5-Fluoro-2-(4-iodo-2-methyl-phenylamino)-phenyl]-[4-(2-hydroxythyl)-piperazin-1-;
N-(3-Diethylamino-2-hydroxy-propyi)-5-fluoro-2-(4-iodo-2-methyl-phenylamino)-benzamide;
N-Cyclopropyl-5-fluoro-2-(4-iodo-2-methyl-phenylamino)-benzamide;
5-Chloro-N-(2-hydroxy-ethyl)-2-(4-iodo-2-methyl-phenylamino)-benzamide;
5-Fluoro-N-2-hydroxy-ethyo)-2-(4iodo-2-methyl-phenylamino)-benzamide;
N-Benyloxy-5-fluoro-2-(4-iodo-2-methyl-phenylamino)-benzamide;
N-Benzyloxy-5-bromo-2-(4-iodo-2-methyl-phenylamino)-benzamide;
2-(4-Iodo-2-methyl-phenylamino)-5-nitro-N-(4-sulfamoyl-benzyl)-benzamide;
5-Bromo-N-(2-hydroxy-ethyl)-2-(4-iodo-2-methyl-phenylamino)-benzamide;
5 N-2-Hydro5ythyl)-5-iodo-2-4iodo-2-methyl-phenylamino)-benzamide;
N-(2-Hydroxy-ethyl)-2-(4-iodo-2-ethyl-phenylamino)-5-nitro-benzamide;
2-(4-Iodo-2-methyl-phenylamino)-N-methyl-5-nitro-N-phenyl-benzamide;
5-Chloro-N-cyclopropyl-2-(4-iodo-2-methyl-phenylamino)-benzamide;
5-Fluoro-2-(4-iodo-2-methyl-phenylamino)-N-methyl-N-phenyl-benzamide;
N-Allyl-5-fluoro-2-(4-iodo-2-methyl-phenylamino)-benzamide;
N-Benzyloxy-5-iodo-2-(4-iodo-2-methyl-phenylamino)-benzaminde;
5-Fluoro-2-(4-iodo-2-methyl-phenylamino)-N-(4-sulfamoyl-benzyl)-benzamide;
N-Allyl-5-chloro-2-(4iodo-2-methyl-phenylamino)-benzamide;
N-Cyclopropyl-2-(4iodo-2-methyl-phenylamino)5-nitro-benzamide;
5-Bromo-N-cyclopropyl-2-(4-iodo-2-methyl-phenylamino)-benzamide;
5-Chloro-2-4-iodo-2-methyl-phenylamino)-N-methyl-N-phenyl-benzamide;
5-Iodo-2-(4-iodo-2-methyl-phenylamino)-N-(4-sulfarmoyl-benzyl)-benzamide;
5-Bromo-2-(4-iodo-2-methyl-phenylamino)-N-(4-sulfamoyl-benzyl)-benzamide;
N-Allyl-2-(4-iodo-2-methyl-phenylamino)-5-nitro-benzamide;
2-(4-lodo-2-methyl-phenylamino)-5-nitro-N-(4-sulfamoyl-benzyl)-benzamide;
N-Allyl-5-bromo-2-(4-iodo-2-methyl-phenylamino)-benzamide;
5-Fluoro-2-(4iodo-2-methyl-phenylamino)-N-(3-methyl-benzyl)-benzamide;
N-Cyclopropyl-5-iodo-2-(4-iodo-2-methyl-phenylamino)-benzamide;
5-Bromo-2-(4-iodo2-methyl-phenylamino)-N-methyl-N-phenyl-benzamide;
N-Benzyloxy-2-(4-iodo-2-methyl-phenylam ino)-5-nitro-benzamide;
N-Cyclohexyl-5-iodo-2-(4-iodo-2-methyl-phenylamino)-benzamide;
N-Allyl-5-iodo-2-(4-iodo-2-methyl-phenylamino)-benzamide;
5-Iodo-2-(4-iodo-2-methyl-phenylamino)-N-(3-methyl-benzyl)-benzamide;
2-(4-Iodo-2-methyl-phenylamino)-N-(3-methyl-benzyl)-5-nitro-benzamide;
5-Iodo-2-(4-iodo-2-methyl-phenylamino)-N-methyl-N-phenyl-benzamide;
N-Cyclohexyl-5-fluoro-2-(4-iodo-2-methyl-phenylamino)-benzamide;
5-Chloro-N-cyclohexyl-2-(4-iodo-2-methyl-phenylamino)-benzamide;
5-Bromo-2-(4-iodo-2-methyl-phenylamino)-N-(3-methyl-benzyl)-benzamide;
5-Bromo-N-yclohexyl-2-(4-iodo-2-methyl-phenylamino)-benzamide;
5-Chloro-2-(4iodo-2-methyl-phenylamino)-N-(3-methyl-benzyl)-benzamide;
N-Cyclohexyl-2-(4-iodo-2-methyl-phenylamino)-5-nitro-benzamide;
N-Benzyloxy-5-bromo-2-(4-iodo-2-methyl-phenylamino)-benzamide;
N-Benzyloxy-5-fluoro-2-(4-iodo-2-methyl-phenylamino)-benzamide;
5-Chloro-N-(2-hydroxy-ethyl)2-(4-iodo-2-methyl-phenylamino)-benzamide;
5-Bromo-N-(2-hydroxy-ethyl)-2-(4iodo-2-methyl-phenylamino)-benzamide;
2-(4-Iodo-2-methyl-phenylamino)-N-methyl-5-nitro-N-phenyl-benzamide;
5-Chloro-2-(4-iodo-2-methyl-phenylamino)-N-methyl-N-phenyl-benzamide;
N-(2-Hydroxy-ethyl)-5-iodo-2-(4iodo-2-methyl-phenylamino)-benzamnide;
5-Chloro-N-cyclopropyl-2-(4-iodo-2-methyl-phenylamino)-benzamide;
N-Allyl-5-chloro-2-(4-iodo-2-methyl-phenylamino)-benzamide;
5-Fluoro-2-(4-iodo-2-methyl-phenylamino)-N-methyl-N-phenyl-benzamide;
N-(2-Hydroxy-ethyl)-2-(4-iodo-2-methyl-phenylamino)-5-nitro-benzamide;
5-Fluoro-N-(2-hydroxy-ethyl)-2-(4-iodo-2-methyl-phenylamino)-benzamide;
5-Bromo-N-cyclopropyl-2-(4-iodo-2-methyl-phenylamino)-benzamide;
N-Cyclopropyl-5-fluoro-2-(4-iodo-2-methyl-phenylamino)-benzamide;
5-Fluoro-2-4-iodo-2-methyl-phenylamino)-N-4-sulfamoyl-benzyl)-benzamide;
N-Cyclopropyl-2-(4-iodo-2-methyl-phenylamino)-5-nitro-benzamide;
N-Allyl-5-fluoro-2-4-iodo-2-methyl-phenylamino)-benzamide;
N-Benzyloxy-5-iodo-2-(4-iodo-2-methyl-phenylamino)-benzamide;
N-Allyl-5-bromo-2-(4-iodo-2-methyl-phenylamino)-benzamide;
5-Bromo-2-(4-iodo-2-methyl-phenylamino)-N-(4-sulfamoyl-benzyl)-benzamide;
5-Bromo-2-(4-iodo-2-methyl-phenylamino)-N-methyl-N-phenyl-benzamide;

N-Allyl-2-(4-iodo-2-methyl-phenylamino)-5-nitro-benzamide;
4-Fluoro-2-(4-iodo-2-methyl-phenylamino)-benzyl alcohol;
[5-Chloro-2-4-iodo-2-methyl-phenylamino)-phenyl]-methanol;
[2-(4-Iodo-2-methyl-phenylamino)-5-nitro-phenyl]-methanol;
[5-Bromo-2-(4-iodo-2-methyl-phenylamino)-phenyl]-methanol; or
N-Allyl-2-(4iodo-2-methyl-phenylamino)-5-nitro-benzamide.

In another preferred embodiment, the MEK inhibitor is a compound of Formula II

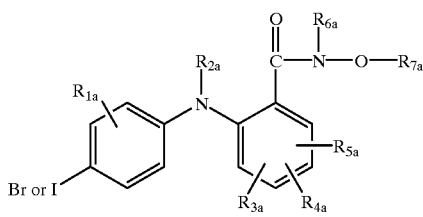

II wherein:
$R_{1a}$ is hydrogen, hydroxy, $C_1$–$C_8$ alkyl, $C_1$–$C_8$ alkoxy, halo, trifluoromethyl, or CN;
$R_{2a}$ is hydrogen;
$R_{3a}$, $R_{4a}$, and $R_{5a}$ independently are hydrogen, hydroxy, halo, trifluoromethyl, $C_1$–$C_8$ alkyl, $C_1$–$C_8$ alkoxy, nitro, CN, or (O or NH)$_m$—(CH$_2$)$_n$—$R_{9a}$, where $R_{9a}$ is hydrogen, hydroxy, CO$_2$H or $NR_{10a}R_{11a}$.
n is 0–4;
m is 0 or 1;
$R_{10a}$ and $R_{11a}$ independently are hydrogen or $C_1$–$C_8$ alkyl or taken together with the nitrogen to which they are attached can complete a 3- to 10-member cyclic ring optionally containing one, two, or three additional heteroatoms selected from O, S, NH, or N—$C_1$–$C_8$ alkyl;
$R_{6a}$ is hydrogen, $C_1$–$C_8$ alkyl,

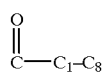

alkyl, aryl, aralkyl, or $C_3$–$C_{10}$ cycloalkyl;
$R_{7a}$ is hydrogen, $C_1$–$C_8$ alkyl, $C_2$–$C_8$ alkenyl, $C_2$-$C_8$ alkynyl, $C_3$–$C_{10}$ (cycloalkyl or cycloalkyl optionally containing a heteroatom selected from O, S, or $NR_{9a}$);
and wherein any of the foregoing alkyl, alkenyl, and alkynyl groups can be unsubstituted or substituted by cycloalkyl, aryl, aryloxy, heteroaryl, or heteroaryloxy; or $R_{6a}$ and $R_{7a}$ taken together with the N to which they are attached can complete a 5- to 10-membered cyclic ring, optionally containing one, two, or three additional heteroatoms selected from O, S, or $NR_{10a}R_{11a}$, and the pharmaceutically acceptable salts, esters, amides or prodrugs thereof.

In a more preferred embodiment the MEK inhibitor is
4-Fluoro-N-hydroxy-2-(4-iodo-2-methyl-phenylamino) benzamide;
4-Fluoro-2-(4-iodo-2-methyl-phenylamino)-N-(methoxy)-benzamide;
4-Fluoro-2-(4-iodo-2-methyl-phenylamino)-N-(prop-2-ynyloxy)-benzamide;
4-Fluoro-2-(4-iodo-2-methyl-phenylamino)-N-(2-phenoxyethoxy)-benzamide;
4-Fluoro-2-(4-iodo-2-methyl-phenylamino)-N-(2-thienylmethoxy)-benzamide;
4-Fluoro-2-(4-iodo-2-methyl-phenylamino)-N-(prop-2-enyloxy)-benzamide;
4-Fluoro-2-(4-iodo-2-methyl-phenylamino)-N-(cyclopropylmethoxy)-benzamide;
4-Fluoro-2-(4-iodo-2-methyl-phenylamino)-N-(cyclopentoxy)-benzamide;
3,4-Difluoro-2-(4-iodo-2-methyl-phenylamino)-N-(3-furylmethoxy)0benzamide;
3,4-Difluoro-2-(4-iodo-2-methyl-phenylamino)-N-ethoxy-benzamide;
3,4-Difluoro-2-(4iodo-2-methyl-phenylamino)-N-(but-2-enyloxy)-benzamide;
3,4-Difluoro-2-(4-iodo-2-methyl-phenylamino)-N-(cyclopropyl-methoxy)-benzamide;
3,4Difluoro-2-(4-iodo-2-methyl-phenylamino)-N-(1-methylprop-2-ynyloxy)-benzamide;
3,4-Difluoro-2-(4-iodo-2-methyl-phenylamino)-N-(3-phenylprop-2-ynyloxy)-benzamide;
3,4-Difluoro-2-(4-iodo-2-methyl-phenylamino)-N-(3-methyl-5-phenylpent-2-en-4ynyloxy)-benzamide;
3,4-Difluoro-2-(4-iod6-2-methyl-phenylamino)-N(prop-2-ynyloxy)-benzamide;
3,4-Difluoro-2-(4-iodo-2-methyl-phenylamino)-N-(propoxy)-benzamide;
3,4-Difluoro-2-4-iodo-2-methyl-phenylamino)-N-(cyclobutyloxy)-benzamide;
3,4-Difluoro-2-(4iodo-2-methyl-phenylamino)-N-(2-thienylmethoxy)-benzamide;
3,4-Difluoro-2(4-iodo-2-methyl-phenylamino)-N-(2-methyl-prop-2-enyloxy)-benzamide;
3,4-Difluoro-2-(4-iodo-2-methyl-phenylamino)-N-(2-phenoxyethoxy)-benzamide;
3,4-Difluoro-2-(4-iodo-2-methyl-phenylamino)-N-(but-2-enyloxy)-benzamide;
3,4-Difluoro-2(4iodo-2-methyl-phenylamino)-N-(but-3-ynyloxy)-benzamide;
3,4-Difluoro-2-(4-iodo-2-methyl-phenylamino)-N-(cyclopentyloxy)-benzamide;
3,4-Difluoro-2-(4-iodo-2-methyl-phenylamino)-N-(3-(2-fluorophenyl)-prop-2-ynyloxy)-benzamide;
5-Bromo-3,4-difluoro-N-hydroxy-2-(4-iodo-2-methyl-phenylamino)-benzamide;
5-Bromo-3,4-difluoro-2-(4iodo-2-methyl-phenylamino)-N-(n-propoxy)-benzamide;
5-Bromo-3,4-difluoro-N-(firan-3-ylmethoxy)-2-(4-iodo-2-methyl-phenylamino)-benzamide;
5-Bromo-N-(but-2-enyloxy)-3,4-difluoro-2-(4-iodo-2-methyl-phenylamino)-benzamide
5-Bromo-N-butoxy-3,4-difluoro-2-(4-iodo-2-methyl-phenylamino)-benzamide;
5-Bromo-3,4-difluoro-2-(4-iodo-2-methyl-phenylamino)-N-(3-methyl-but-2-enyloxy)-benzamide;
5-Bromo-3,4-difluoro-2-(4-iodo-2-methyl-phenylamino)-N-(3-methyl-pent-2-en-4-ynyloxy)-benzamide;

5-Bromo-3,4-difluoro-2-(4-iodo-2-methyl-benzyl)-N-[5-(3-methoxy-phenyl)-3-methyl-pent-2-en-4-ynyloxy]-benzamide;

5-Bromo-3,4-dfluoro-2-(4-iodo-2-methyl-phenylamino)-N-(prop-2-ynyloxy)-benzamide;

5-Bromo-3,4difluoro-2-4-iodo-2-methyl-phenylamino)-N-[3-(3-methoxy-phenyl)-prop-2-ynyloxy]-benzamide;

5-Bromo-3,4-difluoro-2-(4-iodo-2-methyl-phenylamino)-N-(thiopen-2-ylmethoxy)-benzamide;

5-Bromo-3,4-difluoro-2-(4-iodo-2-methyl-phenylamino)-N-(pyridin-3-ylmethoxy)-benzamide;

5-Bromo-34difluoro-2-(4-iodo-2-methyl-phenylamino)-N-(3-2-fluorophenyl)-prop-2-ynyloxy)-benzamide;

5-Bromo-3,4-difluoro-24-iodo-2-methyl-phenylamino)-N-(ethoxy)-benzamide;

5-Bromo-3,4-difluoro-2-(4-iodo2-methyl-phenylamino)-N-(cyclopropylmethoxy)-benzamide;

5-Bromo-3,4-difluoro-2-(4-iodo-2-methyl-phenylamino)-N-(isopropoxy)-benzamide;

5-Bromo-3,4-difluoro-2-(4-iodo-2-methyl-phenylamino)-N-but-3-ynyloxy)-benzamide;

5-Chloro-N-hydroxy-2-(4-iodo-2-methyl-phenylamino)-benzamide;

5-Chloro-2-(4-iodo-2-methyl-phenylamino)-N-(tetrahydro-pyran-2-yloxy)-benzamide;

5-Chloro-2-(4-iodo-2-methyl-phenylamino)-N-methoxy-benzamide;

4-Bromo-2-(4-iodo-2-methyl-phenylamino)N-phenylmethoxy-benzamide;

4-Fluoro-2-(4-iodo-2-methyl-phenylamino)N-phenylmethoxy-benzamide;

5-Fluoro-N-hydroxy-2-(4-iodo-2-methyl-phenylamino)-benzamide;

5-Iodo-2-(4-iodo-2-methyl-phenylamino)-N-phenylmethoxy-benzamide;

5-Fluoro-2(4-iodo-2-methyl-phenylamino)-N-(tetrahydropyran-2-yloxy)-benzamide;

3,4-Difluoro-2-4bromo-2-methyl-phenylamino)-N-(3-phenylprop-2-ynyloxy)-benzamide;

3,4-Difluoro-2-(4-bromo-2-methyl-phenylamino)-N-(3-furylmethoxy)-benzamide;

3,4-Difluoro-2-(4-bromo-2-methyl-phenylamino)-N-(2-thienylmethoxy)-benzamide;

3,4-Difluoro-2-(4-bromo-2-methyl-phenylamino)-N-(but-3-ynyloxy)-benzamide;

3,4-Difluoro-2-(4-bromo-2-methyl-phenylamino)-N-(2-methyl-prop-2-enyloxy)-benzamide;

3,4-Difluoro-2-(4bromo-2-methyl-phenylamino)-N-(but-2-enyloxy)-benzamide;

3,4-Difluoro-2(4-bromo-2-methyl-phenylamino)-N-(methoxy)-benzamide;

3,4-Difluoro-2-(4-bromo-2-methyl-phenylamino)-N-(ethoxy)-benzamide;

3,4-Difluoro-2-(4-bromo-2-methyl-phenylamino)-N-(cyclobutoxy)-benzamide;

3,4-Difluoro-2-(4-bromo-2-methyl-phenylarnino)-N-(isopropoxy)-benzamide;

3,4-Difluoro-2-(4-bromo-2-methyl-phenylamino)-N-(2-phenoxyethoxy)-benzamide;

3,4-Difluoro-2-(4-bromo-2-methyl-phenylamino)-N-(cyclopropyl-methoxy)-benzamide;

3,4-Difluoro-2-(4-bromo-2-methyl-phenylamino)-N-(n-propoxy)-benzamide;

3,4-Difluoro-2-(4-bromo-2-methyl-phenylamino)N-(1-methyl-prop-2-ynyloxy)-benzamide;

3,4-Difluoro-2-(4-broino-2-methyl-phenylamino)-N-(3-(3-fluorophenyl)-prop-2-ynyloxy)-benzamide;

3,4-Difluoro-2-(4-bromo-2-methyl-phenylamnino)-N-(4,4-dimethylpent-2-ynyloxy)-benzamide;

3,4-Difluoro-2-(4-bromo-2-methyl-phenylamino)N-(cyclopentoxy)benzamide;

3,4,5-Trifluoro-N-hydroxy-2-(4-iodo-2-methyl-phenylamino)-benzamide;

5-Chloro-3,4-difluoro-N-hydroxy-2-(4-iodo-2-methyl-phenylamino)-benzamide;

5-Bromo-3,4difluoro-2-(2-fluoro-4-iodo-phenylamino)-N-hydroxy-benzamide;

N-Hydroxy-2-(4iodo-2-methyl-phenylamino)-4-nitro-benzamide;

3,4,5-Trifluoro-2-2-fluoro-4-iodo-phenylamino)-N-hydroxy-benzamide;

5-Chloro-3,4-difluoro-2-(2-fluoro-4-iodo-phenylamino)-N-hydroxy-benzamide;

5-Bromo-2-(2-chloro4-iodo-phenylamino)-3,4-difluoro-N-hydroxy-benzamide;

2-(2-Fluoro-4iodo-phenylamino)-N-hydroxy4nitro-benzamide;

2-(2-Chloro-4-iodo-phenylamino)-3,4,5-trifluoro-N-hydroxy-benzamide;

5-Chloro-2-(2-chloro4-iodo-phenylamino)-3,4-difluoro-N-hydroxy-benzamide;

5-Bromo-2-(2-bromo-4-iodo-phenylamino)-3,4-difluoro-N-hydroxy-benzamide;

2-(2-Chloro-4-iodo-phenylamino)-N-hydroxy4-methyl-benzamide;

2-(2-Bromo-4-iodo-phenylamino)-3,4,5-trifluoro-N-hydroxy-benzamide;

2-2-Bromo-4-iodo-phenylamino)-5-chloro-3,4-difluoro-N-hydroxy-benzamide;

2-(2-Bromo4-iodo-phenylamino)-N-hydroxy4-nitro-benzamide;

4-Fluoro2-(2-fluoro4-iodo-phenylamino)-N-hydroxy-benzamide;

3,4-Difluoro-2-(2-fluoro-4-iodo-phenylamino)-N-hydroxy-benzamide;

2-(2-Chloro-4-iodo-phenylamino)-4-fluoro-N-hydroxy-benzamide;

2-(2-Chloro-4-iodo-phenylamino)3,4difluoro-N-hydroxy-benzamide;

2-(2-Bromo-4-iodo-phenylarnino)4-fluoro-N-hydroxy-benzamide;

2-(2-Bromo-4-iodo-phenylamino)-3,4-difluoro-N-hydroxy-benzamide;

N-Cyclopropylmethoxy-3,4,5-trifluoro-2-(4-iodo-2-methyl-phenylamino)-benzamide;

5-Chloro-N-cyclopropylmethoxy-3,4-difluoro-2-(4-iodo-2-methyl-phenylamino)-benzamide;

5-Bromo-N-cyclopropylmethoxy-3,4-difluoro-2-(2-fluoro4 1iodo-phenylamino)-benzamide;

N-Cyclopropylmethoxy-2-(4-iodo-2-methyl-phenylamino)-4-nitro-benzamide;

N-Cyclopropylmethoxy-3,4,5-trifluoro-2-(2-fluoro-4-iodo-phenylamino)benzamide;

5-Chloro-N-cyclopropylmethoxy-3,4-difluoro-2-(2-fluoro4iodo-phenylamino)-benzamide;

5-Bromo-2-(2-chloro-4-iodo-phenylamino)-N-cyclopropylmethoxy-3,4-difluoro-benzamide;

N-Cyclopropylmethoxy-2-(2-fluoro-4-iodo-phenylamino)4-nitro-benzamide;

2-(2-Chloro-4-iodo-phenylamino)-N-cyclopropylmethoxy-3,4,5-trifluoro-benzamide;

5-Chloro-2-(2-chloro4-iodo-phenylamino)-N-cyclopropylmethoxy-3,4-difluoro-benzamide;

5-Bromo-2-(2-bromo4-iodo-phenylamino)-N-ethoxy-3,4-difluoro-benzamide;

2-(2-Chloro-4-iodo-phenylamino)-N-ethoxy4-nitro-benzamide;

2-(2-Bromo-4-iodo-phenylamino)-N-cyclopropylmethoxy-3,4,5-trifluoro-benzamide;

2-(2-Bromo-4-iodo-phenylanino)5-chloro-N-cyclopropylmethoxy-3,4-difluoro-benzamide 2-(2-Bromo-4-iodo-phenylamino)N-cyclopropylmethoxy4-nitro-benzamide;

N-Cyclopropylmethoxy4-fluoro-2-(2-fluoro4-iodo-phenylamino)-benzamide;

N-Cyclopropylmethoxy-3,4difluoro-2-(2-fluoro-4-iodo-phenylamino)-benzamide;

2-(2-Chloro-4-iodo-phenylamino)-N-cyclopropylmethoxy4-fluoro-benzamide;

2-(2-Chloro-4iodo-phenylamino)-N-cyclopropylmethoxy-3,4-difluoro-benzamide;

2-2-Bromo4iodo-phenylamino)-N-cyclopropylmethoxyfluoro-benzamide; or 2-(2-Bromo-4iodo-phenylamino)-N-cyclopropylmethoxy-3,4difluoro-bennamide.

DETAILED DESCRIPTION OF THE INVENTION

The present invention provides a method of treating or preventing septic shock, the method comprising administering to a patient having septic shock or at risk of having septic shock a therapeutically acceptable amount of a compound that is a MEK inhibitor.

The patients of the present invention have septic shock or are at risk of having septic shock. Those skilled in the art are readily able to identify patients having septic shock. M oreover, patients who are at risk of having septic shock are also easily identifiable by those skilled in the art. For example, patients who are at risk of having septic shock generally comprise patients who have a bacterial infection. Moreover, the bacterial infection is typically a gram-negative bacterial infection.

The term "patient" means all animals including humans. Examples of patients include humans, cows, dogs, cats, goats, sheep, and pigs.

The compounds of the present invention, which can be used to treat septic shock, are MEK inhibitors. A MEK inhibitor is a compound that shows MEK inhibition when tested in the assays titled "Enzyme Assays" in U.S. Pat. No. Number 5,525,625, column 6, beginning at line 35. The complete disclosure of U.S. Pat. No. 5,525,625 is hereby incorporated by reference. An example of a MEK inhibitor is 2-(2-amino-3-methoxyphenyl)-4-oxo-4H-[1]benzopyran. Specifically, a compound is a MEK inhibitor if a compound shows activity in the assay titled "Cascade Assay for Inhibitors of the MAP Kinase, Pathway," column 6, line 36 to column 7, line 4 of the U.S. Pat. No. 5,525,625 and/or shows activity in the assay titled "In Vitro MEK Assay" at column 7, lines 4 to 27 of the above-referenced patent.

The MEK inhibitors of the present method can be administered to a patient as part of a pharmaceutically acceptable composition. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar—agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofIrfbryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalamic formulations, eye ointments, powders, and solutions are also contemplated as being within the scope of this invention.

The compounds of the present method can be administered to a patient at dosage levels in the range of about 0.1 to about 1000 mg per day. For a normal human adult having a body weight of about 70 kg, a dosage in the range of about 0.01 to about 100 mg per kg of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

The compounds of the present method can be administered as pharmaceutically acceptable salts, esters, amides, or prodrugs. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium and the like, as well as nontoxic anmmonium, quaternary ammoniurn, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present method can exist in unsolvated as well as solvated forms with pharmaceutically acceptable solvents such as water, ethanol, and the like. In general, the solvated forms are considered equivalent to the unsolvated forms for the purposes of the present invention.

The compounds of the present method can exist in different stereoisometric forms by virtue of the presence of asymmetric centers in the compounds. It is contemplated that all stereoisometric forms of the compounds as well as mixtures thereof, including racemic mixtures, form part of this invention.

As used herein, the term "aryl" means a cyclic, bicyclic, or tricyclic aromatic ring moiety having from five to twelve carbon atoms. Examples of typical aryl groups include phenyl, naphthyl, and fluorenyl. The aryl may be substituted by one, two, or three groups selected from fluoro, chloro, bromo, iodo, alkyl, hydroxy, alkoxy, nitro, amino, alkylamino, or dialkylamino. Typical substituted aryl groups include 3-fluorophenyl, 3,5-dimethoxyphenyl, 4-nitronaphthyl, 2-methyl-4-chloro-7-aminofluorenyl, and the like.

The term "aryloxy" means an aryl group bonded through an oxygen atom, for example phenoxy, 3-bromophenoxy, naphthyloxy, and 4-methyl-1-fluorenyloxy.

"Heteroaryl" means a cyclic, bicyclic, or tricyclic aromatic ring moiety having from four to eleven carbon atoms and one, two, or three heteroatoms selected from O, S, or N. Examples include furyl, thienyl, pyrrolyl, pyrazolyl, imidazolyl, triazolyl, thiazolyl, oxazolyl, xanthenyl, pyronyl, indolyl, pyrimidyl, naphthyridyl, pyridyl, benzinnidazolyl, and triazinyl. The heteroaryl groups can be unsubstituted or substituted by one, two, or three groups selected from fluoro, chloro, bromo, iodo, alkyl, hydroxy, alkoxy, nitro, amino, alkylamino, or dialkylamino. Examples of substituted heteroaryl groups include chloropyranyl, methylthienyl, fluoropyridyl, amino-1,4-benzisoxazinyl, nitroisoquinolinyl, and hydroxyindolyl.

The heteroaryl groups can be bonded through oxygen to make heteroaryloxy groups, for example thienyloxy, isothiazolyloxy, benzofuranyloxy, pyridyloxy, and 4-methylisoquinolinyloxy.

The term "alkyl" means straight and branched chain aliphatic groups. Typical alkyl groups include methyl, ethyl, isopropyl, terl-butyl, 2,3-dimethylhexyl, and 1,1-dimethylpentyl. The alkyl groups can be unsubstituted or substituted by halo, hydroxy, alkoxy, amino, alkylamino, dialkylamino, cycloalkyl, aryl, aryloxy, heteroaryl, or heteroaryloxy, as those terms are defined herein. Typical substituted alkyl groups include chloromethyl, 3-hydroxypropyl, 2-dimethylaminobutyl, and 2-(hydroxymethylamino)ethyl. Examples of aryl and aryloxy substituted alkyl groups include phenylmethyl, 2-phenylethyl, 3-chlorophenylmethyl, 1,1-dimethyl-3-(2-nitrophenoxy)butyl, and 3,4,5-trifluoronaphthylmethyl. Examples of alkyl groups substituted by a heteroaryl or heteroaryloxy group include thienylmethyl, 2-fuirylethyl, 6-furyloxyoctyl, 4-methylquinolyloxymethyl, and 6-isothiazolylhexyl. Cycloalkyl substituted alkyl groups include cyclopropylmethyl, 2-cyclohexyethyl, piperidyl-2-methyl, 2-(piperidin-1-yl)-ethyl, 3-(morpholin-4-yl)propyl.

"Alkenyl" means a straight or branched carbon chain having one or more double bonds. Examples include but-2-enyl, 2-methyl-prop-2-enyl, 1,1-dimethyl-hex4-enyl, 3-ethyl-4-methyl-pent-2-enyl, and 3-isopropyl-pent-1-enyl. The alkenyl groups can be substituted with halo, hydroxy, alkoxy, amino, alkylamino, dialkylamino, aryl, aryloxy, heteroaryl, or heteroyloxy, for example 2-bromoethenyl, 3-hydroxy-2-butenyl, 1-aminoethenyl, 3-phenylprop-2-enyl, 6-thienyl-hex-2-enyl, 2-furyloxy-but-2-enyl, and 4-naphthyloxy-hex-2-enyl.

"Alkynyl" means a straight or branched carbon chain having at least one triple bond. Typical alkynyl groups include prop-2-ynyl, 2-methyl-hex-5-ynyl, 3,4-dimethyl-hex-5-ynyl, and 2-ethyl-but-3-ynyl. The alkynyl groups can be substituted as the alkyl and alkenyl groups, for example, by aryl, aryloxy, heteroaryl, or heteroaryloxy, for example 4-(2-fluorophenyl)-but-3-ynyl, 3-methyl-5-thienylpent4-ynyl, 3-phenoxy-hex4-ynyl, and 2-furyloxy-3-methyl-hex-4-ynyl.

The alkenyl and alkynyl groups can have one or more double bonds or triple bonds, respectively, or a combination of double and triple bonds. For example, typical groups having both double and triple bonds include hex-2-en-4-ynyl, 3-methyl-5-phenylpent-2-en4-ynyl, and 3-thienyloxy-hex-3-en-5-ynyl.

The term "cycloalkyl" means a nonaromatic ring or fused rings. Examples include cyclopropyl, cyclobutyl, cyclopenyl, cyclooctyl, bicycloheptyl, adamantyl, and cyclohexyl. The ring can optionally contain one, two, or three heteroatoms selected from O, S, or N. Such groups include tetrahydrofuryl, tetrahydropyrrolyl, octahydrobenzofilranyl, morpholinyl, piperazinyl, pyrrolidinyl, piperidinyl, octahydroindolyl, and octahydrobenzothiofiranyl. The cycloalkyl groups can be substituted with the same substituents as an alkyl and alkenyl groups, for example, halo, hydroxy, aryl, and heteroaryloxy. Examples include 3-hydroxycyclohexyl, 2-aminocyclopropyl, 2-phenylpyrrolidinyl, and 3-thienylmorpholine-1-yl.

The examples presented below are intended to illustrate particular embodiments of the invention and are not intended to limit the scope of the specification, including the claims, in any way.

The 2-(4-bromo and 4-iodo phenylamino)-benzoic acid derivatives of Formula I can be prepared from commercially available starting materials utilizing synthetic methodologies well-known to those skilled in organic chemistry. A typical synthesis is carried out by reacting a 4-bromo or 4-iodo aniline with a benzoic acid having a leaving group at the 2-position to give a 2-(phenylamino)-benzoic acid. This process is depicted in Scheme 1.

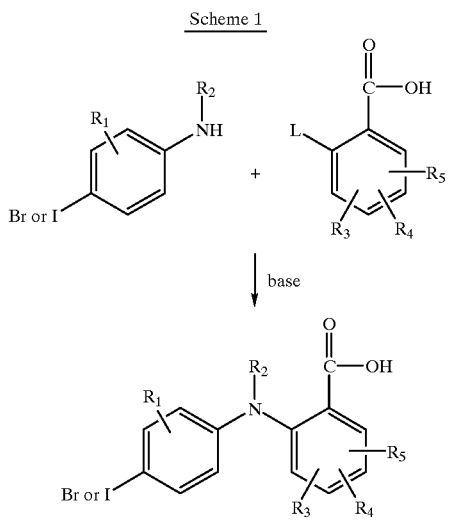

Scheme 1 where L is a leaving group, for example halo such as fluoro.

The reaction of aniline and the benzoic acid derivative generally is accomplished by mixing the benzoic acid with an equimolar quantity or excess of the aniline in an unreactive organic solvent such as tetrahydroflian or toluene, in the presence of a base such as lithium diisopropylamide, n-butyl lithium, sodium hydride, triethylamine, and Hunig's base. The reaction generally is carried out at a temperature of about −78° C. to about 100° C., and normally is complete within about 2 hours to about 4 days. The product can be isolated by removing the solvent, for example by evaporation under reduced pressure, and further purified, if desired, by standard methods such as chromatography, crystallization, or distillation.

The 2-(phenylamino)-benzoic acid (e.g., Formula I, where $R_7$ is hydrogen) can be reacted with an organic or inorganic base such as pyridine, triethylamine, calcium carbonate, or sodium hydroxide to produce a pharmaceutically acceptable salt. The free acids can also be reacted with an alcohol of the formula $HOR_7$ (where $R_7$ is other than hydrogen, for example methyl) to produce the corresponding ester. Reaction of the benzoic acid with an alcohol can be carried out in the presence of a coupling agent. Typical coupling reagents include 2-ethoxy-1-ethoxycarbonyl-1,2-dihydroquinoline (EEDQ), 1,3-dicyclohexylcarbodiimide (DCC), bromo-tris(pyrrolidino)- phosphonium hexafluorophosphate (PyBrOP), and (benzotriazolyloxy) tripyrrolidino phosphonium hexafluorophosphate (PyBOP). The phenylamino benzoic acid and alcohol derivative normally are mixed in approximately equimolar quantities in an unreactive organic solvent such as dichloromethane, tetrahydrofuran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol.

The benzamides of the invention, Formula I where Z is $CONR_6R_7$, are readily prepared by reacting the foregoing benzoic acids with an amine of the formula $HNR_6R_7$. The reaction is carried out by reacting approximately equimolar quantities of the benzoic acid and amine in an unreactive organic solvent in the presence of a coupling reagent. Typical solvents are chloroform, dichloromethane, tetrahydrofiran, benzene, toluene, and xylene. Typical coupling reagents include DCC, EEDQ, PyBrOP, and PYBOP. The reaction is generally complete after about 10 minutes to about 2 hours when carried out at a temperature of about 0° C. to about 60° C. The product amide is readily isolated by removing the reaction solvent, for instance by evaporation, and firther purification can be accomplished by normal methods such as chromatography, crystallization, or distillation. The hydrazides ($z=CONHNR_{10}R_{11}$) are similarly prepared by coupling a benzoic acid with a hydrazine of the formula $H_2HNR_{10}R_{11}$.

The benzyl alcohols of the invention, compounds of Formula I where Z is $CH_2OR_6$ and $R_6$ is hydrogen, are readily prepared by reduction of the corresponding benzoic acid according to the following scheme

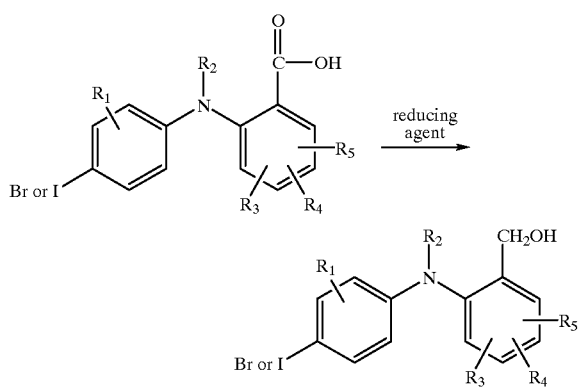

Typical reducing agents commonly employed include borane in tetrahydrofuran. The reduction normally is carried out in an unreactive organic solvent such as tetrahydrofuran, and generally is complete within about 2 hours to about 24 hours when conducted at a temperature of about 0° C. to about 40° C.

The following detailed examples illustrate specific compounds provided by this invention.

EXAMPLE 1

4-Fluoro-2-(4-iodo-2-methylyhenylamino)benzoic acid

To a stirring solution comprised of 3.16 g (0.0133 mol) of 2-amino-5-iodotoluene in 5 mL of tetrahydrofuiran at −78° C. was added 10 mL (0.020 mol) of a 2.0 M lithium diisopropylamide in tetrahydrofuran/heptane/ethenylbenzene (Aldrich) solution. The resulting green suspension was stirred vigorously for 15 minutes, after which time a solution of 1.00 g (0.00632 mol) of 2,4-difluorobenzoic acid in 10 mL of tetrahydrofliran was added. The reaction temperature was allowed to increase slowly to room temperature, at which temperature it was stirred for 2 days. The reaction mixture was concentrated. Aqueous HCl (10%) was added to the concentrate, and the solution was extracted with dichloromethane. The organic phase was dried ($MgSO_4$) and then boiled over a steambath to low volume and cooled to room temperature. The off-white fibers were collected by vacuum filtration, rinsed with hexanes, and vacuum-oven dried. (76° C.; ca. 10 mm of Hg) to afford 1.10 g (47%) of the desired material; mp 224–229.5° C.;

$^1$HNMR (400 MHz; DMSO): δ 9.72 (s, 1H), 7.97 (dd, 1H, J=7.0, 8.7 Hz), 7.70 (d, 1H, J=1.5 Hz), 7.57 (dd, 1H, J=8.4, 1.9 Hz), 7.17 (d, 1H, J=8.2 Hz), 6.61–6.53 (m, 2H), 2.18 (s, 3H);

$^{13}$C NMR (100 MHz; DMSO): δ 169.87, 167.60, 165.12, 150.17, 150.05, 139.83, 138.49, 136.07, 135.31, 135.20, 135.07, 125.60, 109.32, 105.09, 104.87, 99.72, 99.46, 89.43, 17.52;

$^{19}$F NMR (376 MHz; DMSO): δ −104.00 to −104.07 (m); IR (KBr) 1670 (C=O stretch) $cm^{-1}$;
MS (CI) M+1=372.
Analysis calculated for $C_{14}H_{11}FINO_2$:
C, 45.31; H, 2.99; N, 3.77.
Found: C, 45.21; H, 2.77; N, 3.64.

EXAMPLES 2–30

By following the general procedure of Example 1, the following benzoic acids and salts were prepared:

| Example No. | Compound | MP ° C. |
|---|---|---|
| 2 | 3,4,5-Trifluoro-2-(4-iodo-2-methyl-phenylamino)-benzoic acid | 206–210 |
| 3 | 3,4-Difluoro-2-(4-iodo-2-methyl-phenylamino)-benzoic acid | 240.5–244.5 |
| 4 | 5-Bromo-3,4-difluoro-2-(4-iodo-2-methyl-phenylamino)-benzoic acid | 259.5–262 |
| 5 | 5-Chloro-2-(2-chloro-4-iodo-phenylamino)-benzoic acid | 255–260 |
| 6 | 5-Chloro-2-(4-iodo-2-methyl-phenylamino)-benzoic acid | 234–238 |
| 7 | Sodium 5-Chloro-2-(4-iodo-2-methyl-phenylamino)-benzoate | 310–320 DEC |
| 8 | 5-Bromo-2-(4-iodo-2-methyl-phenylamino)-benzoic acid | 239.5–240 |

-continued

| Example No. | Compound | MP ° C. |
|---|---|---|
| 9 | 2-(2-Chloro-4-iodo-phenylamino)-5-nitro-benzoic acid | 289–293 |
| 10 | 4-Fluoro-2-(3-fluoro-4-iodo-2-methyl-phenylamino)-benzoic acid | 233–235 |
| 11 | 2-(4-Iodo-2-methyl-phenylamino)-5-nitro-benzoic acid | 264–267 |
| 12 | 2-(2-Fluoro-4-iodo-phenylamino)-5-nitro-benzoic acid | 256–258 |
| 13 | 2-(4-Bromo-2-methyl-phenylamino)-4-fluoro-benzoic acid | 218.5–220 |
| 14 | 2-(2-Bromo-4-iodo-phenylamino)-5-nitro-benzoic acid | 285–288 DEC |
| 15 | 2-(4-Bromo-2-methyl-phenylamino)-3,4-difluoro-benzoic acid | 230–234 |
| 16 | 3-Fluoro-2-(4-iodo-2-methyl-phenylamino)-benzoic acid | 218–221 |
| 17 | 3,4-Difluoro-2-(4-iodo-2-methoxy-phenylamino)-benzoic acid | 230–233 |
| 18 | 4-Chloro-2-(4-iodo-2-methyl-phenylamino)-benzoic acid | 245–255 DEC |
| 19 | 2-(4-Iodo-2-methyl-phenylamino)-benzoic acid | 218–223 |
| 20 | 5-Fluoro-2-(4-iodo-2-methyl-phenylamino)-benzoic acid | 243–46 |
| 21 | 5-Iodo-2-(4-iodo-2-methyl-phenylamino)-benzoic acid | 241–245 |
| 22 | 2,3,5-Trifluoro-4-(4-iodo-2-methyl-phenylamino)-benzoic acid | 218–222 |
| 23 | 4-Fluoro-2-(3-chloro-4-iodo-2-methyl-phenylamino)-benzoic acid | 248–252.5 |
| 24 | 2-(4-Iodo-phenylamino)-5-methoxy-benzoic acid | 208–211 |
| 25 | 3-Chloro-2-(2-chloro-4-iodo-phenylamino)-benzoic acid | 232–233 |
| 26 | 2-Fluoro-6-(4-iodo-2-methyl-phenylamino)-benzoic acid | 179–182 |
| 27 | 4-Fluoro2-(2,3-dimethyl-4-iodo-2-methyl-phenylamino)benzoic acid | 258–261 |
| 28 | 5-Methyl-2-(4-iodo-2-methyl-phenylamino)-benzoic acid | 209.5–211 |
| 29 | 2-Chloro-6-(4-iodo-2-methyl-phanylamino)-benzoic acid | 171–175 |
| 30 | 2-(4-Iodo-2-methyl-phenylamino)-4-nitro-benzoic acid | 251–263 |

EXAMPLE 31

5-Chloro-N-(2-hydroxyethy-2-(4iodo-2-methyl-phenylamino)-benzamide

To a stirring solution comprised of 0.1020 g (0.2632 mmol) of 5-chloro-2-methyl-phenylamino)-benzoic acid, 0.1 mL (1.7 mmol) of ethanolamine, and 0.05 mL (0.29 mmol) of diisopropylethylamine in 5 mL of a 1:1 (v/v) tetrahydrofuran-dichloromethane solution was added 0.15 g (0.29 mmol) of solid PyBOP powder directly. The reaction mixture was stirred at room temperature overnight. The solvent was removed in vacuo. The crude residue was partitioned between ether (50 mL) and 10% aqueous hydrochloric acid (50 mL). The organic phase was washed with 10% aqueous sodium hydroxide (50 mL), dried (MgSO$_4$) and concentrated in vacuo to afford a yellow-brown oil which was crystallized from hexanes-ether to afford 0.0831 g (73%) of a green-yellow powder; mp 120–121° C.;
$^1$H NMR (400 MHz; CDCl$_3$): δ 9.11 (s, 1H), 7.56 (d, 1H, J=1.4 Hz), 7.46–7.41 (m, 2H), 7.20 (dd, 1H, J=8.9, 2.4 Hz), 7.00 (t, 2H, J=9.6 Hz), 6.55 (broad t, 1H), 3.86 (t, 2H, J=5.0 Hz), 3.61 (dd, 2H, J=10.1, 5.5 Hz), 2.23 (s, 3H), 1.56 (broad s, 1H);
IR (KBr) 3297 (O-H stretch), 1627 (C=O stretch) cm$^{-1}$;
MS (CI) M+1=431.
Analysis calculated for C$_{16}$H$_{16}$ClIN$_2$O$_2$: C, 44.62; H, 3.74; N, 6.50.
Found: 44.63; H, 3.67; N, 6.30.

EXAMPLES 32–48

By following the general procedure of Example 31, the following benzamides were prepared by reacting the corresponding benzoic acid with the corresponding amine.

| Example No. | Compound | MP ° C. |
|---|---|---|
| 32 | 4-Methoxy-N-(4-methoxy-phenyl)-3-nitro-benzamide | 153.5–156 |
| 33 | 4-Fluoro-2-(4-iodo-2-methyl-phenylamino)-benzamide | 158 |
| 34 | 4-Fluoro-2-(4-iodo-2-methyl-phenylamino)-N-methyl-benzamide | 102.5–104.5 |
| 35 | N-Ethyl-4-fluoro-2-(4-iodo-2-methyl-phenylamino)-benzamide | 90–91 |
| 36 | 4-Fluoro-2-(4-iodo-2-methyl-phenylamino)-N,N-dimethyl-benzamide | oil |
| 37 | 4-Fluoro-2-(4-iodo-2-methyl-phenylamino)-N-(1H-tetrazol-5-yl)-benzamide | 285–288 DEC |
| 38 | 5-Bromo-2-(4-iodo-2-methyl-phenylamino)-benzamide | 180–182 |
| 39 | 5-Chloro-2-(4-iodo-2-methyl-phenylamino)-N,N-dimethyl-benzamide | 137–138 |
| 40 | [5-Chloro-2-(4-iodo-2-methyl-phenylamino)-benzoylamino]-acetic acid | 170–173 |
| 41 | 4-Fluoro-2-(4-iodo-2-methyl-phenylamino)-N-propyl-benzamide | 69–71 |
| 42 | 5-Bromo-N-(2-hydroxy-ethyl)-2-(4-iodo-2-methyl-phenylamino)-benzamide | 132–133.4 |
| 43 | N,N-Diethyl-4-fluoro-2-(4-iodo-2-methyl-phenylamino)-benzamide | oil |
| 44 | 4-Fluoro-N-{3-[4-(2-hydroxy-ethyl)-piperazin-1-yl]-propyl}-2-(4-iodo-2-methyl-phenylamino)-benzamide | 122–124 |
| 45 | N,N-Diethyl-2-(4-iodo-2-methyl-phenylamino)-5-nitro-benzamide | 91–93 |
| 46 | N-Butyl-4-fluoro-2-(4-iodo-2-methyl-phenylamino)-benzamide | 97–99 |
| 47 | 5-Chloro-N,N-diethyl-2-(4-iodo-2-methyl-phenylamino)-benzamide | 118–120 |
| 48 | 5-Bromo-2-(4-iodo-2-methyl-phenylamino)-N,N-dimethyl-benzamide | 142.5–144 |

EXAMPLE 49

4-Fluoro-2-(4-iodo-2-methyl-phenylamino)-benzyl alcohol

4-Fluoro-2-(4-iodo-2-methyl-phenylamino)-benzoic acid (0.50 g, 1.35 mmol) was dissolved in 6 mL (6 mmol) of cold 1.0 M borane-tetrahydrofuran complex in tetrahydrofuran solution. The reaction mixture was stirred under nitrogen atmosphere at room temperature overnight. The reaction was quenched with 80 mL of methanol. Concentration in vacuo produced a clear tan oil which was purified by MPLC. Elution with dichloromethane afforded 0.4285 g (89%) of a white solid; mp 99–100.5° C.;
$^1$H NMR (400 MHz; DMSO): δ 7.57 (d, 1H, J=1.7 Hz), 7.45 (dd, 1H, J=8.4, 1.9 Hz), 7.39 (s, 1H), 7.29 (t, 1H, J=7.5 Hz), 6.89 (d, 1H, J=8.4 Hz), 6.67–6.60 (m, 1H), 5.47 (t, 1H, J=5.5 Hz), 4.49 (d, 2H, 5.1 Hz), 2.14 (s, 3H);
IR (KBr) 3372 (O-H stretch) cm$^{-1}$;
MS (CI) M+1=358.
Analysis calculated for C$_{14}$H$_{13}$FINO:

C, 47.08; H, 3.67; N, 3.92.
Found: C, 47.17; H, 3.75; N, 3.72.

EXAMPLE 50–52

The following benzyl alcohols were prepared by the general procedure of Example 49.

| Example No. | Compound | MP ° C. |
|---|---|---|
| 50 | [5-Chloro-2-(4-iodo-2-methyl-phenylamino)-phenyl]-methanol | 82–85 |
| 51 | [2-(4-Iodo-2-methyl-phenylamino)-5-nitro-phenyl]-methanol | 126.5–128.5 |
| 52 | [5-Bromo-2-(4-iodo-2-methyl-phenylamino)-phenyl]-methanol | 60.5–63.5 |

Several invention compounds of Formula I were prepared utilizing combinatorial synthetic techniques. The general procedure is as follows:

To a 0.8-mL autosampler vial in a metal block was added 40 μL of a 0.5 M solution of the acid in DMF and 40 μL of the reagent amine (2 M solution in Hunig's base and 1 M in amine in DMF). A 0.5 M solution of PyBrop was freshly prepared and 50 μL were added to the autosampler vial. The reaction was allowed to stand for 24 hours.

The reaction mixture was transferred to a 2-dram vial and diluted with 2 mL of ethyl acetate. The organic layer was washed with 3 mL of distilled water and the water layer washed again with 2 mL of ethyl acetate. The combined organic layers were allowed to evaporate to dryness in an open fume hood.

The residue was taken up in 2 mL of 50% acetonitrile in water and injected on a semi-prep reversed phase column (10 mm×25 cm, 5 μM spherical silica, pore size 115 A derivatized with C-18, the sample was eluted at 4.7 mulmin with a linear ramp to 100% acetonitrile over 8.5 minutes. Elution with 100% acetonitrile continued for 8 minutes). Fractions were collected by monitoring at 214 nM. The residue was dissolved in chloroform and transferred to a preweighed vial, evaporated, and weighed again to determine the yield.

EXAMPLES 53–206

The following compounds of Formula I were prepared by combinatorial methodology:

| Example No. | Compound | MS M-H |
|---|---|---|
| 53 | 5-Bromo-3,4-difluoro-N-(2-hydroxy-ethyl)-2-(4-iodo-2-methyl-phenylamino)-benzamide | 510 |
| 54 | N-(2,3-Dihydroxy-propyl)-3,4-difluoro-2-(4-iodo-2-methyl-phenylamino)-benzamide | 462 |
| 55 | 5-Bromo-3,4-difluoro-2-(4-iodo-2-methyl-phenylamino)-N-(2-piperidin-1-yl-ethyl)-benzamide | 577 |
| 56 | 3,4-Difluoro-N-(2-hydroxy-ethyl)-2-(4-iodo-2-methyl-phenylamino)-benzamide | 432 |
| 57 | N-(2,3-Dihydroxy-propyl)-4-fluoro-2-(4-iodo-2-methyl-phenylamino)-benzamide | 444 |
| 58 | 3,4-Difluoro-N-(3-hydroxy-propyl)-2-(4-iodo-2-methyl-phenylamino)-benzamide | 446 |
| 59 | 5-Bromo-3,4-difluoro-2-(4-iodo-2-methyl-phenylamino)-N-(2-pyrrolidin-1-yl-ethyl)-benzamide | 564 |
| 60 | 5-Bromo-3,4-difluoro-2-(4-iodo-2-methyl-phenylamino)-N-(2-pyridin-4-yl-ethyl)-benzamide | 571 |
| 61 | 4-Fluoro-N-(2-hydroxy-ethyl)-2-(4-iodo-2-methyl-phenylamino)-benzamide | 414 |
| 62 | 5-Bromo-N-(3-dimethylamino-propyl)-3,4-difluoro-2-(4-iodo-2-methyl-phenylamino)-benzamide | 551 |
| 63 | 5-Bromo-3,4-difluoro-2-(4-iodo-2-methyl-phenylamino)-N-(2-morpholin-4-ethyl)-benzamide | 580 |
| 64 | 3,4-Difluoro-2-(4-iodo-2-methyl-phenylamino)-N-(2-morpholin-4-yl-ethyl)-benzamide | 501 |
| 65 | 3,4-Difluoro-2-(4-iodo-2-methyl-phenylamino)-N-(2-pyrrolidin-1-yl-ethyl)-benzamide | 485 |
| 66 | 3,4-Difluoro-2-(4-iodo-2-methyl-phenylamino)-N-(2-pyridin-4-yl-ethyl)-benzamide | 493 |
| 67 | N-(3-Dimethylamino-propyl)-3,4-difluoro-2-(4-iodo-2-methyl-phenylamino)-benzamide | 473 |
| 68 | N-Benzyl-4-fluoro-2-(4-iodo-2-methyl-phenylamino)-benzamide | 460 |
| 69 | 2-(4-Bromo-2-methyl-phenylamino)-3,4-difluoro-N-(2-hydroxy-ethyl)-benzamide | 384 |
| 70 | 4-Fluoro-2-(4-iodo-2-methyl-phenylamino)-N-(2-morpholin-4-yl-ethyl)-benzamide | 483 |
| 71 | 4-Fluoro-2-(4-iodo-2-methyl-phenylamino)-N-(3-piperidin-1-yl-propyl)-benzamide | 495 |
| 72 | 3,4-Difluoro-2-(4-iodo-2-methyl-phenylamino)-N-(3-piperidin-1-yl-propyl)-benzamide | 513 |
| 73 | 4-Fluoro-2-(4-iodo-2-methyl-phenylamino)-N-(2-thiophen-2-yl-ethyl)-benzamide | 480 |
| 74 | 4-Fluoro-2-(4-iodo-2-methyl-phenylamino)-N-(2-pyrrolidin-1-yl-ethyl)-benzamide | 467 |
| 75 | 2-(4-Bromo-2-methyl-phenylamino)-3,4-difluoro-N-(2-morpholin- | 453 |

-continued

| Example No. | Compound | MS M-H |
|---|---|---|
| | 4-yl-ethyl)-benzamide | |
| 76 | 5-Bromo-3,4-difluoro-2-(4-iodo-2-methyl-phenylamino)-N-pyridin-4-ylmethyl-benzamide | 557 |
| 77 | 3,4-Difluoro-2-(4-iodo-2-methyl-phenylamino)-N-pyridin-4-ylmethyl-benzamide | 479 |
| 78 | 2-(4-Bromo-2-methyl-phenylamino)-N-(3-dimethylamino-propyl)-3,4-difluoro-benzamide | 425 |
| 79 | 4-Fluoro-2-(4-iodo-2-methyl-phenylamino)-N-pyridin-4-ylmethyl-benzamide | 461 |
| 80 | 4-Fluoro-2-(4-iodo-2-methyl-phenylamino)-N-(2-pyridin-4-yl-ethyl)-benzamide | 475 |
| 81 | 2-(4-Bromo-2-methyl-phenylamino)-3,4-difluoro-N-(2-pyridin-4-yl-ethyl)-benzamide | 445 |
| 82 | 2-(4-Bromo-2-methyl-phenylamino)-3,4-difluoro-N-(3-hydroxy-propyl)-benzamide | 400 |
| 83 | 2-(4-Bromo-2-methyl-phenylamino)-3,4-difluoro-N-(2-pyrrolidin-1-yl-ethyl)-benzamide | 437 |
| 84 | 4-Fluoro-2-(4-iodo-2-methyl-phenylamino)-N-phenethyl-benzamide | 474 |
| 85 | 2-(4-Bromo-2-methyl-phenylamino)-3,4-difluoro-N-(2-thiophen-2-yl-ethyl)-benzamide | 450 |
| 86 | 2-(4-Bromo-2-methyl-phenylamino)-3,4-difluoro-N-pyridin-4-ylmethyl-benzamide | 431 |
| 87 | 2-(4-Bromo-2-methyl-phenylamino)-3,4-difluoro-N-phenethyl-benzamide | 444 |
| 88 | 2-(4-Bromo-2-methyl-phenylamino)-3,4-difluoro-N-(2-piperidin-1-yl-ethyl)-benzamide | 451 |
| 89 | 5-Chloro-N-{3-[4-(2-hydroxy-ethyl)-piperazin-1-yl]-propyl}-2-(4-iodo-2-methyl-phenylamino)-benzamide | 557* |
| 90 | 5-Fluoro-N-{3-[4-(2-hydroxy-ethyl)-piperazin-1-yl]-propyl}-2-(4-iodo-2-methyl-phenylamino)-benzamide | 541* |
| 91 | 2-(4-Iodo-2-methyl-phenylamino)-5-nitro-N-pyridin-4-yl methyl-benzamide | 487 |
| 92 | 5-Bromo-N-{3-[4-(2-hydroxyethyl)-piperazin-1-yl]-propyl}-2-(4-iodo-2-methyl-phenylamino)-benzamide | 601* |
| 93 | 5-Chloro-N-(2-diethylamino-ethyl)-2-(4-iodo-2-methyl-phenylamino)-benzamide | 486* |
| 94 | 5-Chloro-2-(4-iodo-2-methyl-phenylamino)-N-(2-piperidin-1-yl-ethyl)-benzamide | 497* |
| 95 | (3-Hydroxy-pyrrolidin-1-yl)-[2-(4-iodo-2-methyl-phenylamino)-5-nitro-phenyl]- | 466 |
| 96 | 5-Chloro-2-(4-iodo-2-methyl-phenylamino)-N-(2-pyrrolidin-1-yl-ethyl)-benzamide | 484* |
| 97 | 5-Bromo-N-(2-diethylamino-ethyl)-2-(4-iodo-2-methyl-phenylamino)-benzamide | 530* |
| 98 | N-{2-[Bis-(2-hydroxy-ethyl)-amino]-ethyl}-5-chloro-2-(4-iodo-2-methyl-phenylamino)-benzamide | 518* |
| 99 | N-{2-[Bis-(2-hydroxy-ethyl)-amino]-ethyl}-5-bromo-2-(4-iodo-2-methyl-phenylamino)-benzamide | 562* |
| 100 | [5-Bromo-2-(4-iodo-2-methyl-phenylamino)-phenyl]-(3-hydroxy-pyrrolidin-1-yl)- | 499 |
| 101 | 2-(4-Iodo-2-methyl-phenylamino)-5-nitro-benzoic acid phenethyl ester | 501 |
| 102 | N-{3-[4-(2-Hydroxy-ethyl)-piperazin-1-yl]-propyl}-2-(4-iodo-2-methyl-phenylamino)-benzamide | 568* |
| 103 | [5-Chloro-2-(4-iodo-2-methyl-phenylamino)-phenyl]-(3-hydroxy-pyrrolidin-1-yl)- | 455 |
| 104 | 5-Fluoro-2-(4-iodo-2-methyl-phenylamino)-N-pyridin-4-ylmethyl-benzamide | 460 |
| 105 | 5-Bromo-2-(4-iodo-2-methyl-phenylamino)-N-(2-pyrrolidin-1-yl-ethyl)-benzamide | 528* |
| 106 | 5-Bromo-2-(4-iodo-2-methyl-phenylamino)-N-(2-piperidin-1-yl-ethyl)-benzamide | 542* |
| 107 | 5-Fluoro-2-(4-iodo-2-methyl-phenylamino)-N-(2-pyrrolidin-1-yl-ethyl)-benzamide | 468* |
| 108 | 5-Chloro-N-(3-dimethylamino-propyl)-2-(4-iodo-2-methyl-phenylamino)-benzamide | 472* |
| 109 | N-{2-[Bis-(2-hydroxy-ethyl)-amino]-ethyl}-5-fluoro-2-(4-iodo-2-methyl-phenylamino)-benzamide | 502* |
| 110 | 5-Chloro-N-(3-hydroxy-propyl)-2-(4-iodo-2-methyl-phenylamino)-benzamide | 445* |
| 111 | 5-Chloro-N-(3-diethylamino-2-hydroxy-propyl)-2-(4-iodo-2-methyl-phenylamino)-benzamide | 516* |
| 112 | 5-Fluoro-2-)(4-iodo-2-methyl-phenylamino)-N-(2-piperidin-1-yl-ethyl)-benzamide | 482* |
| 113 | 5-Bromo-N-(3-hydroxy-propyl)-2-(4-iodo-2-methyl- | 489* |

-continued

| Example No. | Compound | MS M-H |
|---|---|---|
| | phenylamino)-benzamide | |
| 114 | 5-Bromo-2-(4-iodo-2-methyl-phenylamino)-N-(3-piperidin-1-yl-propyl)-benzamide | 556* |
| 115 | N-{2-[Bis-(2-hydroxy-ethyl)-amino]-ethyl}-2-(4-iodo-2-methyl-phenylamino)-5-nitro-benzamide | 529* |
| 116 | 5-Chloro-2-(4-iodo-2-methyl-phenylamino)-N-(2-morpholin-4-yl-ethyl)-benzamide | 500* |
| 117 | 5-Chloro-N-(3-diethylamino-propyl)-2-(4-iodo-2-methyl-phenylamino)-benzamide | 500* |
| 118 | 5-Chloro-N-(2-diisopropylamino-ethyl)-2-(4-iodo-2-methyl-phenylamino)-benzamide | 514* |
| 119 | 5-Chloro-2-(4-iodo-2-methyl-phenylamino)-N-(3-piperidin-1-yl-propyl)-benzamide | 512* |
| 120 | 2-(4-Iodo-2-methyl-phenylamino)-5-nitro-N-(2-piperidin-1-yl-ethyl)-benzamide | 509* |
| 121 | 5-Bromo-2-(4-iodo-2-methyl-phenylamino)-N-(2-piperazin-1-yl-ethyl)-benzamide | 544* |
| 122 | N-(2-Diethylamino-ethyl)-5-fluoro-2-(4-iodo-2-methyl-phenylamino)-benzamide | 470* |
| 123 | 5-Bromo-N-(3-dimethylamino-propyl)-2-(4-iodo-2-methyl-phenylamino)-benzamide | 516* |
| 124 | N-(3-Hydroxy-propyl)-2-(4-iodo-2-methyl-phenylamino)-5-nitro-benzamide | 456* |
| 125 | 5-Fluoro-N-(3-hydroxy-propyl)-2-(4-iodo-2-methyl-phenylamino)-benzamide | 429* |
| 126 | N-(3-Diethylamino-propyl)-5-fluoro-2-(4-iodo-2-methyl-phenylamino)-benzamide | 484* |
| 127 | N-(3-Diethylamino-propyl)-2-(4-iodo-2-methyl-phenylamino)-5-nitro-benzamide | 511* |
| 128 | 5-Bromo-2-(4-iodo-2-methyl-phenylamino)-N-(2-morpholin-4-yl-ethyl)-benzamide | 544* |
| 129 | 2-(4-Iodo-2-methyl-phenylamino)-5-nitro-N-(3-piperidin-1-yl-propyl)-benzamide | 523* |
| 130 | [5-Fluoro-2-(4-iodo-2-methyl-phenylamino)-phenyl]-(3-hydroxy-pyrrolidin-1-yl)- | 439 |
| 131 | 5-Bromo-N-(2-diisopropylamino-ethyl)-2-(4-iodo-2-methyl-phenylamino)-benzamide | 558* |
| 132 | 5-Fluoro-2-(4-iodo-2-methyl-phenylamino)-N-(2-morpholin-4-yl-ethyl)-benzamide | 484* |
| 133 | 5-Fluoro-2-(4-iodo-2-methyl-phenylamino)-N-(3-piperidin-1-yl-propyl)-benzamide | 496* |
| 134 | [5-fluoro-2-(4-iodo-2-methyl-phenylamino)-phenyl]-[4-(2-hydroxy-ethyl)-piperazin-1- | 482 |
| 135 | N-(3-Diethylamino-2-hydroxy-propyl)-5-fluoro-2-(4-iodo-2-methyl-phenylamino)-benzamide | 500* |
| 136 | [5-Chloro-2-(4-iodo-2-methyl-phenylamino)-benzoylamino]-acetic acid | 443 |
| 137 | 2-(4-Iodo-2-methyl-phenylamino)-5-nitro-N-(2-pyrrolidin-1-yl-ethyl)-benzamide | 495* |
| 138 | N-(3-Dimethylamino-propyl)-2-(4-iodo-2-methyl-phenylamino)-5-nitro-benzamide | 483* |
| 139 | N-(2-Diisopropylamino-ethyl)-5-fluoro-2-(4-iodo-2-methyl-phenylamino)-benzamide | 498* |
| 140 | 5-Fluoro-2-(4-iodo-2-methyl-phenylamino)-thiobenzoic acid S-phenethyl ester | 490 |
| 141 | 5-Chloro-2-(4-iodo-2-methyl-phenylamino)-thiobenzoic acid S-phenethyl ester | 506 |
| 142 | 5-Bromo-2-(4-iodo-2-methyl-phenylamino)-thiobenzoic acid S-benzyl ester | 536 |
| 143 | 2-(4-Iodo-2-methyl-phenylamino)-5-nitro-thiobenzoic acid S-benzyl ester | 503 |
| 144 | 5-Fluoro-2-(4-iodo-2-methyl-phenylamino)-thiobenzoic acid S-benzyl ester | 476 |
| 145 | 5-Chloro-2-(4-iodo-2-methyl-phenylamino)-thiobenzoic acid S-benzyl ester | 492 |
| 146 | N-Cyclopropyl-5-fluoro-2-(4-iodo-2-methyl-phenylamino)-benzamide | 409 |
| 147 | 5-Chloro-N-(2-hydroxy-ethyl)-2-(4-iodo-2-methyl-phenylamino)-benzamide | 429 |
| 148 | 5-Fluoro-N-(2-hydroxy-ethyl)-2-(4-iodo-2-methyl-phenylamino)-benzamide | 413 |
| 149 | N-Benzyloxy-5-fluoro-2-(4-iodo-2-methyl-phenylamino)-benzamide | 475 |
| 150 | N-Benzyloxy-5-bromo-2-(4-iodo-2-methyl-phenylamino)-benzamide | 593* |
| 151 | 2-(4-Iodo-2-methyl-phenylamino)-5-nitro-N-(4-sulfamoyl-benzyl)- | 567 |

-continued

| Example No. | Compound | MS M-H |
|---|---|---|
| | benzamide | |
| 152 | 5-Bromo-N-(2-hydroxy-ethyl)-2-(4-iodo-2-methyl-phenylamino)-benzamide | 473 |
| 153 | N-(2-Hydroxy-ethyl)-5-iodo-2-(4-iodo-2-methyl-phenylamino)-benzamide | 521 |
| 154 | N-(2-Hydroxy-ethyl)-2-(4-iodo-2-methyl-phenylamino)-5-nitro-benzamide | 440 |
| 155 | 2-(4-Iodo-2-methyl-phenylamino)-N-methyl-5-nitro-N-phenyl-benzamide | 486 |
| 156 | 5-Chloro-N-cyclopropyl-2-(4-iodo-2-methyl-phenylamino)-benzamide | 425 |
| 157 | 5-Fluoro-2-(4-iodo-2-methyl-phenylamino)-N-methyl-N-phenyl-benzamide | 459 |
| 158 | N-Allyl-5-fluoro-2-(4-iodo-2-methyl-phenylamino)-benzamide | 409 |
| 159 | N-Benzyloxy-5-iodo-2-(4-iodo-2-methyl-phenylamino)-benzamide | 583 |
| 160 | 5-Fluoro-2-(4-iodo-2-methyl-phenylamino)-N-(4-sulfamoyl-benzyl-benzamide | 538 |
| 161 | N-Allyl-5-chloro-2-(4-iodo-2-methyl-phenylamino)-benzamide | 425 |
| 162 | N-Cyclopropyl-2-(4-iodo-2-methyl-phenylamino)-5-nitro-benzamide | 436 |
| 163 | 5-Bromo-N-cyclopropyl-2-(4-iodo-2-methyl-phenylamino)-benzamide | 469 |
| 164 | 5-Chloro-2-(4-iodo-2-methyl-phenylamino)-N-methyl-N-phenyl-benzamide | 475 |
| 165 | 5-Iodo-2-(4-iodo-2-methyl-phenylamino)-N-(4-sulfamoyl-benzyl)-benzamide | 646 |
| 166 | 5-Bromo-2-(4-iodo-2-methyl-phenylamino)-N-(4-sulfamoyl-benzyl-benzamide | 598 |
| 167 | N-Allyl-2-(4-iodo-2-methyl-phenylamino)-5-nitro-benzamide | 436 |
| 168 | 2-(4-Iodo-2-methyl-phenylamino)-5-nitro-N-(4-sulfamoyl-benzyl)-benzamide | 565 |
| 169 | N-Allyl-5-bromo-2-(4-iodo-2-methyl-phenylamino)-benzamide | 469 |
| 170 | 5-Fluoro-2-(4-iodo-2-methyl-phenylamino)-N-(3-methyl-benzyl)-benzamide | 473 |
| 171 | N-Cyclopropyl-5-iodo-2-(4-iodo-2-methyl-phenylamino)-benzamide | 517 |
| 172 | 5-Bromo-2-(4-iodo-2-methyl-phenylamino)-N-methyl-N-phenyl benzamide | 519 |
| 173 | N-Benzyloxy-2-(4-iodo-2-methyl-phenylamino)-5-nitro-benzamide | 502 |
| 174 | N-Cyclohexyl-5-iodo-2-(4-iodo-2-methyl-phenylamino)-benzamide | 559 |
| 175 | N-Allyl-5-iodo-2-(4-iodo-2-methyl-phenylamino)-benzamide | 517 |
| 176 | 5-Iodo-2-(4-iodo-2-methyl-phenylamino)-N-(3-methyl-benzyl)-benzamide | 581 |
| 177 | 2-(4-Iodo-2-methyl-phenylamino)-N-(3-methyl-benzyl)-5-nitro-benzamide | 500 |
| 178 | 5-Iodo-2-(4-iodo-2-methyl-phenylamino)-N-methyl-N-phenyl-benzamide | 567 |
| 179 | N-Cyclohexyl-5-fluoro-2-(4-iodo-2-methyl-phenylamino)-benzamide | 451 |
| 180 | 5-Chloro-N-cyclohexyl-2-(4-iodo-2-methyl-phenylamino)-benzamide | 467 |
| 181 | 5-Bromo-2-(4-iodo-2-methyl-phenylamino)-N-(3-methyl-benzyl)-benzamide | 533 |
| 182 | 5-Bromo-N-cyclohexyl-2-(4-iodo-2-methyl-phenylamino)-benzamide | 511 |
| 183 | 5-Chloro-2-(4-iodo-2-methyl-phenylamino)-N-(3-methyl-benzyl)-benzamide | 489 |
| 184 | N-Cyclohexyl-2-(4-iodo-2-methyl-phenylamino)-5-nitro-benzamide | 478 |
| 185 | N-Benzyloxy-5-bromo-2-(4-iodo-2-methyl-phenylamino)-benzamide | 538 |
| 186 | N-Benzyloxy-5-fluoro-2-(4-iodo-2-methyl-phenylamino)-benzamide | 477 |
| 187 | 5-Chloro-N-(2-hydroxy-ethyl)-2-(4-iodo-2-methyl-phenylamino)-benzamide | 431 |
| 188 | 5-Bromo-N-(2-hydroxy-ethyl-2-(4-iodo-2-methyl-phenylamino)-benzamide | 475 |
| 189 | 2-(4-Iodo-2-methyl-phenylamino)-N-methyl-5-nitro-N-phenyl-benzamide | 488 |
| 190 | 5-Chloro-2-(4-iodo-2-methyl-phenylamino)-N-methyl-N-phenyl-benzamide | 477 |
| 191 | N-(2-Hydroxy-ethyl)-5-iodo-2-(4-iodo-2-methyl-phenylamino)-benzamide | 523 |
| 192 | 5-Chloro-N-cyclopropyl-2-(4-iodo-2-methyl-phenylamino)- | 425 |

-continued

| Example No. | Compound | MS M-H |
|---|---|---|
| | benzamide | |
| 193 | N-Allyl-5-chloro-2-(4-iodo-2-methyl-phenylamino)-benzamide | 427 |
| 194 | 5-Fluoro-2-(4-iodo-2-methyl-phenylamino)-N-methyl-N-phenyl-benzamide | 461 |
| 195 | N-(2-Hydroxy-ethyl)-2-(4-iodo-2-methyl-phenylamino)-5-nitro-benzamide | 442 |
| 196 | 5-Fluoro-N-(2-hydroxy-ethyl)-2-(4-iodo-2-methyl-phenylamino)-benzamide | 415 |
| 197 | 5-Bromo-N-cyclopropyl-2-(4-iodo-2-methyl-phenylamino)-benzamide | 472 |
| 198 | N-Cyclopropyl-5-fluoro-2-(4-iodo-2-methyl-phenylamino)-benzamide | 411 |
| 199 | 5-Fluoro-2-(4-iodo-2-methyl-phenylamino)-N-(4-sulfamoyl-benzyl)-benzamide | 540 |
| 200 | N-Cyclopropyl-2-(4-iodo-2-methyl-phenylamino)-5-nitro-benzamide | 438 |
| 201 | N-Allyl-5-fluoro-2-(4-iodo-2-methyl-phenylamino)-benzamide | 411 |
| 202 | N-Benzyloxy-5-iodo-2-(4-iodo-2-methyl-phenylamino)-benzamide | 585 |
| 203 | N-Allyl-5-bromo-2-(4-iodo-2-methyl-phenylamino)-benzamide | 472 |
| 204 | 5-Bromo-2-(4-iodo-2-methyl-phenylamino)-N-(4-sulfamoyl-benzyl)-benzamide | 601 |
| 205 | 5-Bromo-2-(4-iodo-2-methyl-phenylamino)-N-methyl-N-phenyl-benzamide | 522 |
| 206 | N-Allyl-2-(4-iodo-2-methyl-phenylamino)-5-nitro-benzamide | 438 |

*M + H

EXAMPLE 207

Preparation of 4-Chloro-2-(1H-tetrazol-5-yl)44-iodo-2-methyl-phenyl)-amine

Step a: Preparation of 5-chloro-2-fluoro-benzaldehyde

To a solution of 1-chloro-4-fluorobenzne (13.06 g, 0.1 mol) in THF (180 mL), at −78° C., LDA (2 M solution in THF, 50 mL, 0.1 mol) was added drop wise. After stirring at −78° C. for 1.5 hours, DMF (8 mL) was added to the reaction mixture and allowed to warm up to room temperature overnight. The reaction mixture was partitioned between water and $Et_2O$. The $Et_2O$ layer was dried ($MgSO_4$) and the solvent removed in vacuum to give 14.95 g (94%) yield of crude aldehyde:

$^1$H NMR ($CDCl_3$): δ 10.3 (s, —C(=O)H.

Step b: Preparation of 5-chloro-2-fluoro-benzaldehade oxime

A solution of 5-chloro-2-fluoro-benzaldehyde (10 g, 0.0631 mol), hydroxylamine hydrochloride (6.57 g, 0.0946 mol) and pyridine (8.3 mL, 0.1010 mol) in EtOH (100 mL) was heated at 75° C. (oil bath temperature) for 1 hour and the solvent removed under vacuum to give an oil. The oil was partitioned between water and $CH_2Cl_2$. The $CH_2Cl_2$ layer was dried ($MgSO_4$) and the solvent removed under vacuum to give crude aldoxime as a solid. The solid was purified by medium pressure liquid chromatography on silica. Elution with $CH_2Cl_2$ gave 4.87 g (28%) of the aldoxime as white solid: mp 95–97° C.;

Analysis calculated for $C_7H_5NOFCl$:

C, 48.44; H, 2.90; N, 8.07.

Found: C, 48.55; H, 2.69, N, 7.90.

Step c: Preparation of 5-chloro-2-fluoro-benzonirile

A solution of the 5-chloro-2-fluoro-benzaldehyde oxime (3.15 g, 0.0182 mol) in acetic anhydride (150 mL) was refluxed for 16 hours. The reaction mixture was cooled to room temperature and poured into saturated aqueous $NaHCO_3$ (200 mL) solution. The mixture was extracted with $Et_2O$. The $Et_2O$ layer was dried ($K_2CO_3$) and the solvent removed to give the product as an oily solid. The product was used without further purification in the next step.

Step d: Preparation of 5(5-chloro-2-fluoro-phenyl)-1H-tetrazole

A mixture of 5-chloro-2-fluoro-benzonitrile (2.84 g, 0.01823 mol), butanol (15 mL), sodium azide (1.543 g, 0.0237 mol), acetic acid (1.36 mL, 0.0237 mol) was refluxed for 24 hours. The reaction mixture was cooled to room temperature, additional 1.543 g sodium azide added, and the reaction mixture refluxed for additional 24 hours. After cooling to room temperature, $Et_2O$ (100 mL) and 10% aqueous NaOH (200 mL) were added sequentially. The mixture was vigorously stirred. The aqueous layer was separated, cooled with ice-methanol bath (−15° C.) and acidified to pH 1 with conc. HCl. A gray solid precipitated. The solid was dried in vacuum at 50° C. to give 1.76 g (49%) of 5-(5-chloro-2-fluoro-phenyl)-1H-tetrazole: mp partial melt at 110° C., complete melting at 124° C.);

$^1$H (400 Mz, $CDCl_3$): δ 8.19–8.08 (m, 1H), 7.77–7.71 (m, 1H), 7.61–7.52 (m, 1H);

$^{13}$C (100 Mz, $CDCl_3$): δ 159.00, 156.49, 140.88, 133.02, 132.93, 130.73, 129.23, 129.21, 129.08, 126.05, 118.96, 118.73, 114.50;

MS (CI) M+1=199 (100), M=198 (6).

Step e: Preparation of [4-Chloro-2-(1H-tetrazol-5-yl)-(4-iodo-2-methyl-phenyl)-amine To a solution of 2-methyl4-iodoaniline (3.52 g, 0.0151 mol) in THF (25 mL) at −78° C., LDA (2 molar solution in THF, 11.33 mL, 0.02267 mol) was added dropwise. After stirring for 0.5 hours, a solution of 1-(tetrazol-5-yl)-2-fluoro-5-chlorobenzene (1.5 g, 0.00756 mol) in THF (15 mL) was added dropwise. The reaction was stirred for 16 hours as it warmed up to room temperature. The reaction mixture was quenched with aqueous conc. $NH_4Cl$ solution and extracted with $CH_2Cl_2$. The organic layer was dried ($MgSO_4$) and the solvent removed giving a crude product as an oil. The oil with $CH_2Cl_2$->$CH_2Cl_2$: MeOH (9.7:0.3) gave 1.5 g (48%) of the desired product:

mp 205–208° C.;

$^1$H (400 Mz, DMSO): δ 9.13 (s, 1H), 8.00–7.99 (s, 1H), 7.69 (s, 1H), 7.55–7.52 (m, 1H), 7.43–7.40 (m, 1H), 7.12–7.05 (m, 1H), 2.24 (s, 3H);

$^{13}$C (100 Mz, $CDCl_3$): δ 141.87, 139.28, 138.88, 135.47, 133.71, 131.65, 128.15, 123.69, 121.94, 116.68, 87.79, 17.22;

MS (CI) M+2=413 (44), M+1=412 (85), M=411 (100).
Analysis calculated for $C_{14}H_{11}N_5ClI \cdot 0.5H_2O$:
  C, 39.97; H, 2.87; N, 16.65.
Found: C, 38.87, H, 2.77; N, 16.47.

The following tetrazole substituted phenylamines were prepared by following the general procedure of Example 207.

EXAMPLE 208

(4-iodo-2-methyl-phenyl)-[2-(1H-tetrazol-5-yl)-phenyl]amine, mp 231° C. (dec)

EXAMPLE 209

[4-nitro-2-(1H-tetrazol-5-yl)-(4-iodo-2-methyl-phenyl)-amine, mp 205–208° C.

The 4-bromo and 4-iodo phenylamino benzhydroxamic acid derivatives of Formula I can be prepared from commercially available starting materials utilizing synthetic methodologies well-known to those skilled in organic chemistry. A typical synthesis is carried out by reacting a 4-bromo or 4-iodo aniline with a benzoic acid having a leaving group at the 2-position to give a phenylamino benzoic acid, and then reacting the benzoic acid phenylamino derivative with a hydroxylamine derivative. This process is depicted in Scheme 1a.

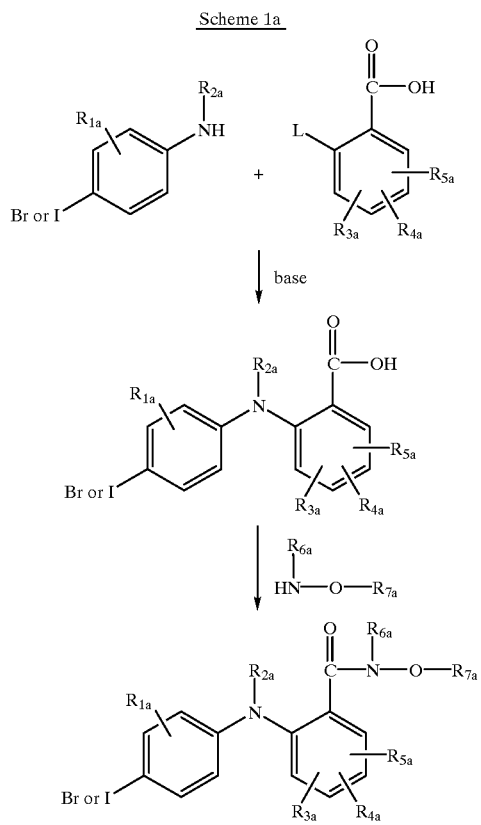

where L is a leaving group, for example halo such as fluoro, chloro, bromo or iodo, or an activated hydroxy group such as a diethylphosphate, trimethylsilyloxy, p-nitrophenoxy, or phenylsulfonoxy.

The reaction of aniline and the benzoic acid derivative generally is accomplished by mixing the benzoic acid with an equimolar quantity or excess of the aniline in an unreactive organic solvent such as tetrahydrofuran, or toluene, in the presence of a base such as lithium diisopropylamide, n-butyl lithium, sodium hydride, and sodium amide. The reaction generally is carried out at a temperature of about −78° C. to about 25° C., and normally is complete within about 2 hours to about 4 days. The product can be isolated by removing the solvent, for example by evaporation under reduced pressure, and further purified, if desired, by standard methods such as chromatography, crystallization, or distillation.

The phenylamino benzoic acid next is reacted with a hydroxylamine derivative $HNR_{6a}OR_{7a}$ in the presence of a peptide coupling reagent. Hydroxylamine derivatives that can be employed include methoxylamine, N-ethyl-isopropoxy amine, and tetrahydro-oxazine. Typical coupling reagents include 2-ethoxy- 1-ethoxycarbonyl-1,2-dihydroquinoline (EEDQ), 1,3-dicyclohexylcarbodiimide (DCC), bromo-tris(pyrrolidino)-phosphonium hexafluorophosphate (PyBrOP) and (benzotriazolyloxy)tripyrrolidino phosphonium hexafluorophosphate (PyBOP). The phenylamino benzoic acid and hydroxylamino derivative normally are mixed in approximately equimolar quantities in an unreactive organic solvent such as dichloromedtane, tetrahydrofiran, chloroform, or xylene, and an equimolar quantity of the coupling reagent is added. A base such as triethylamine or diisopropylethylamine can be added to act as an acid scavenger if desired. The coupling reaction generally is complete after about 10 minutes to 2 hours, and the product is readily isolated by removing the reaction solvent, for instance by evaporation under reduced pressure, and purifying the product by standard methods such as chromatography or crystallizations from solvents such as acetone, diethyl ether, or ethanol.

An alternative method for making the invention compounds involves first converting a benzoic acid to a hydroxamic acid derivative, and then reacting the hydroxamic acid derivative with an aniline. This synthetic sequence is depicted in Scheme 2.

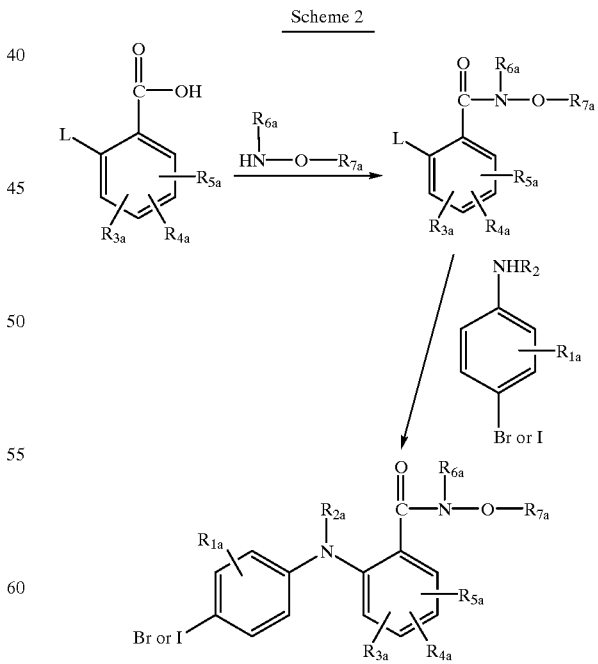

where L is a leaving group. The general reaction conditions for both of the steps in Scheme 2 are the same as those described above for Scheme 1a.

Yet another method for making invention compounds comprises reacting a phenylamino benzhydroxamic acid with an ester forming group as depicted in Scheme 3.

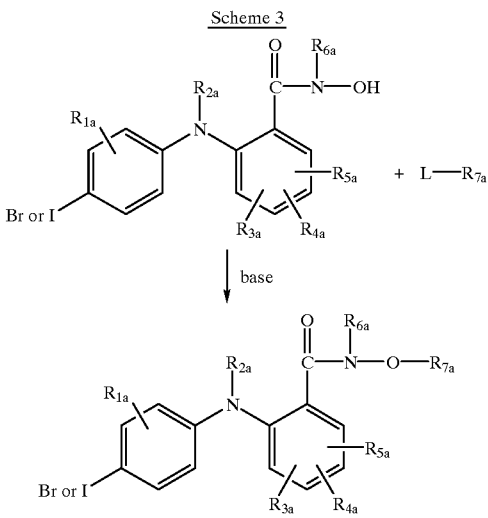

where L is a leaving group such as halo, and a base is triethylamine or diisopropylamine.

The synthesis of invention compounds of Formula II is further illustrated by the following detailed examples.

EXAMPLE 1a

4-Fluoro-N-hydroxy-2-(4-iodo-2-methyl-phenylamino)-benzamide (a) Preparation of 4Fluoro-2-(4iodo-2-methyl-phenylamino)-benzoic acid To a stirred solution containing 3.16 g (0.0133 mol) of 2-amino-5-iodotoluene in 5 mL of tetrahydrofuran at −78° C. was added 10 mL (0.020 mol) of a 2.0 M lithium diisopropylamide in tetrahydrofuran/heptane/ethylbenzene (Aldrich) solution. The resulting green suspension was stirred vigorously for 15 minutes, after which time a solution of 1.00 g (0.00632 mol) of 2,4-difluorobenzoic acid in 10 mL of tetrahydrofuran was added. The reaction temperature was allowed to increase slowly to room temperature, at which temperature the mixture was stirred for 2 days. The reaction mixture was concentrated by evaporation of the solvent under reduced pressure. Aqueous HCl (10%) was added to the concentrate, and the solution was extracted with dichloromethane. The organic phase was dried (MgSO$_4$) and then concentrated over a steambath to low volume (10 mL) and cooled to room temperature. The off-white fibers which formed were collected by vacuum filtration, rinsed with hexane, and dried in a vacuum-oven (76° C.; ca. 10 mm of Hg) to afford 1.10 g (47%) of the desired material; mp 224–229.5° C.;

$^1$H NMR (400 MHz, DMSO): δ 9.72 (s, 1H), 7.97 (dd, 1H, J=7.0, 8.7 Hz), 7.70 (d, 1H, J=1.5 Hz), 7.57 (dd, 1H,.J=8.4, 1.9 Hz), 7.17 (d, 1H, J=8.2 Hz), 6.61–6.53 (m, 2H), 2.18 (s, 3H);

$^{13}$C NMR (100 MHz, DMSO): δ 169.87, 166.36 (d, J$_{C-F}$= 249.4 Hz), 150.11 (d, J$_{C-F}$=11.4 Hz), 139.83, 138.49, 136.07, 135.26 (d, J$_{C-F}$=11.5 Hz), 135.07, 125.60, 109.32, 104.98 (d, J$_{C-F}$=21.1 Hz), 99.54 (d, J$_{C-F}$=26.0 Hz), 89.43, 17.52;

$^{19}$F NMR (376 MHz, DMSO): δ104.00 to −104.07 (m);
IR (KBr) 1670 (C=O stretch)cm$^{-1}$;
MS (CI) M+1=372.
Analysis calculated for C$_{14}$H$_{11}$FINO$_2$:
C, 45.31; H, 2.99; N, 3.77.
Found: C, 45.21; H, 2.77; N, 3.64.

(b) Preparation of 4-Fluoro-N-hydroxy-2-(4-iodo-2-methvl-Rhenvlamino)-benzamide

To a stirred solution of 4-fluoro-2-(4-iodo-2-methyl-phenylamino)-benzoic acid (0.6495 g, 0.001750 mol), O-(tetrahydro-2H-pyran-2-yl)-hydroxylamine (0.2590 g, 0.002211 mol), and diisopropylethylamine (0.40 mL, 0.0023 mol) in 31 mL of an equivolume tetrahydrofuran-dichloromethane solution was added 1.18 g (0.00227 mol) of solid PYBOP ([benzotriazolyloxy]tripyrrolidino phosphonium hexafluorophosphate, Advanced ChemTech) directly. The reaction mixture was stirred for 30 minutes after which time it was concentrated in vacuo. The brown oil was treated with 10% aqueous hydrochloric acid. The suspension was extracted with ether. The organic extraction was washed with 10% sodium hydroxide followed by another 10% hydrochloric acid wash, was dried (MgSO$_4$) and concentrated in vacuo to afford 1.0 g of a light-brown foam. This intermediate was dissolved in 25 mL of ethanolic hydrogen chloride, and the solution was allowed to stand at room temperature for 15 minutes. The reaction mixture was concentrated in vacuo to a brown oil that was purified by flash silica chromatography. Elution with dichloromethane→dichloromethane-methanol (166:1) afforded 0.2284 g of a light-brown viscous oil. Scratching with pentane-hexanes and drying under high vacuum afforded 0.1541 g (23%) of an off-white foam; mp 61–75° C.;

$^1$H NMR (400 MHz, DMSO): δ 11.34 (s, 1H), 9.68 (s, 1H), 9.18 (s, 1H), 7.65 (d, 1H, J=1.5Hz), 7.58 (dd, 1H, J=8.7, 6.8 Hz), 7.52 (dd, 1H, J=8.4, 1.9 Hz), 7.15 (d, 1H, J=8.4 Hz), 6.74 (dd, 1H, J=11.8, 2.4 Hz), 6.62 (ddd, 1H, J=8.4, 8.4, 2.7 Hz), 2.18 (s, 3H);

$^{13}$C NMR (100 MHz, DMSO): δ 165.91, 164.36 (d, J$_{C-F}$= 247.1 Hz), 146.78, 139.18, 138.77, 135.43, 132.64, 130.60 (d, J$_{C-F}$=11.5 Hz), 122.23, 112.52, 104.72 (d, J=22.1 Hz), 100.45 (d, J$_{C-F}$=25.2 Hz), 86.77, 17.03;

$^{19}$F NMR (376 MHz, DMSO): δ −107.20 to −107.27 (m);
IR (KBr) 3307 (broad, O-H stretch), 1636 (C=O stretch) cm$^{-1}$;
MS (CI) M+1=387.
Analysis calculated for C$_{14}$H$_{12}$FIN$_2$O$_2$:
C, 43.54; H, 3.13; N, 7.25.
Found: C, 43.62; H, 3.24; N, 6.98.

EXAMPLE 2a

5-Bromo-3,4-difluoro-N-hydroxy-2-(4-iodo-2-methyl-phenylamino)-benzamide (a) Preparation of 5-Bromo-2,3,4-trifluorobenzoic acid To a stirred solution comprised of 1-bromo-2,3,4-trifluorobenzene (Aldrich, 99%; 5.30 g, 0.0249 mol) in 95 mL of anhydrous tetrahydrofuran cooled to −78° C. was slowly added 12.5 mL of 2.0 M lithium diisopropylamide in heptane/tetrahydrofuran/ethylbenzene solution (Aldrich). The mixture was stirred for 1 hour and transferred by canula into 700 mL of a stirred saturated ethereal carbon dioxide solution cooled to −78° C. The cold bath was removed, and the reaction mixture was stirred for 18 hours at ambient temperature. Dilute (10%) aqueous hydrochloric acid (ca. 500 mL) was poured into the reaction mixture, and the mixture was subsequently concentrated on a rotary evaporator to a crude solid. The solid product was partitioned between diethyl ether (150 mL) and aq. HCl (330 mL, pH 0). The aqueous phase was extracted with a second portion (100 mL) of diethyl ether, and the combined ethereal extracts were washed with 5% aqueous sodium hydroxide (200 mL) and water (100 mL, pH 12). These combined alkaline aqueous extractions were acidified to pH 0 with concentrated aqueous hydrochloric acid. The resulting suspension was extracted with ether (2×200 mL). The combined organic extracts were dried ($MgSO_4$), concentrated in vacuo, and subjected to high vacuum until constant mass was achieved to afford 5.60 g (88% yield) of an off-white powder, mp 139–142.5° C.;
$^1$H NMR (400 MHz, DMSO): δ 13.97 (broad s, 1H, 8.00–7.96 (m, 1H);
$^{13}$C NMR (100 MHz, DMSO): δ 162.96, 129.34,118.47, 104.54 (d, $J_{C-F}$22.9 Hz);
$^{19}$F NMR (376 MHz, DMSO): δ −120.20 to −120.31 (m), −131.75 to −131.86 (m), −154.95 to −155.07 (m);
IR (KBr) 1696 (C=O stretch)$cm^{-1}$;
MS (CI) M+1=255.
Analysis calculated for $C_{74}H_{21}BrF_3O_2$:
  C, 32.97; H, 0.79; N, 0.00; Br, 31.34; F, 22.35.
Found: C, 33.18; H, 0.64; N, 0.01; Br, 30.14; F, 22.75.

(b) Preparation of 5-Bromo-3,4-difluoro-2-(4-iodo-2-methyl-phenylamino)-benzoic acid To a stirred solution comprised of 1.88 g (0.00791 mol) of 2-amino-5-iodotoluene in 10 mL of tetrahydrofuran at −78° C. was added 6 mL (0.012 mol) of a 2.0 M lithium diisopropylamide in tetrahydrofuran/heptane/ethylbenzene (Aldrich) solution. The resulting green suspension was stirred vigorously for 10 minutes, after which time a solution of 1.00 g (0.00392 mol) of 5-bromo-2,3,4-trifluorobenzoic acid in 15 mL of tetrahydrofuran was added. The cold bath was subsequently removed, and the reaction mixture stirred for 18 hours. The mixture was concentrated, and the concentrate was treated with 100 mL of dilute (10%) aqueous hydrochloric acid. The resulting suspension was extracted with ether (2×150 mL), and the combined organic extractions were dried ($MgSO_4$) and concentrated in vacuo to give an orange solid. The solid was triturated with boiling dichloromethane, cooled to ambient temperature, and collected by filtration. The solid was rinsed with dichloromethane, and dried in the vacuum-oven (80° C.) to afford 1.39 g (76%) of a yellow-green powder, mp 259.5–262° C.;
$^1$H NMR (400 MHz, DMSO): δ 9.03 (s, 1H), 7.99 (dd, 1H, J=7.5, 1.9 Hz), 7.57 (dd, 1H, J=1.5 Hz), 7.42 (dd, 1H, J=8.4, 1.9 Hz), 6.70 (dd, 1H, J=8.4, 6.0 Hz), 2.24 (s, 3H);
$^{19}$F NMR (376 MHz, DMSO): δ −123.40 to −123.47 (m); −139.00 to −139.14 (m);
IR (KBr) 1667 (C=O stretch)$cm^{-1}$;
MS (CI) M+1=469.
Analysis calculated for $C_{14}H_9BrF_2INO_2$:
  C, 35.93; H, 1.94; N, 2.99; Br, 17.07; F, 8.12; 1, 27.11.
Found: C, 36.15; H, 1.91; N, 2.70; Br, 16.40; F, 8.46; 1, 26.05.

(c) Preparation of 5-Bromo-3,4-difluoro-N-hydroxy-2-(4-iodo-2-methyl-phenylamino)-benzamide To a stirred solution comprised of 5-bromo-3,4-difluoro-2-(4-iodo-2-methyl-phenylamino)-benzoic acid (0.51 g, 0.0011 mol), O-(tetrahydro-2H-pyran-2-yl)-hydroxylamine (0.15 g, 0.0013 mol), and diisopropylethylamine (0.25 mL, 0.0014 mol) in 20 mL of an equivolume tetrahydrofuran-dichloromethane solution was added 0.6794 g (0.001306 mol) of solid PyBOP (Advanced ChemTech) directly. The reaction mixture was stirred at 24° C. for 10 minutes, and then was concentrated to dryness in vacuo. The concentrate was suspended in 100 mL of 10% aqueous hydrochloric acid. The suspension was extracted with 125 mL of diethyl ether. The ether layer was separated, washed with 75 mL of 10% aqueous sodium hydroxide, and then with 100 mL of dilute acid. The ether solution was dried ($MgSO_4$) and concentrated in vacuo to afford 0.62 g (100%) of an off-white foam. The foam was dissolved in ca. 15 mL of methanolic hydrogen chloride. After 5 minutes, the solution was concentrated in vacuo to an oil, and the oil was purified by flash silica chromatography. Elution with dichloromethane→dichloromethane-methanol (99:1) afforded 0.2233 g (42%) of a yellow powder. The powder was dissolved in diethyl ether and washed with dilute hydrochloric acid. The organic phase was dried ($MgSO_4$) and concentrated in vacuo to afford 0.200 g of a foam. This product was triturated with pentane to afford 0.1525 g of a powder that was repurified by flash silica chromatography. Elution with dichloromethane afforded 0.0783 g (15%) of an analytically pure title compound, mp 80–90° C.;
$^1$H NMR (400 MHz, DMSO): δ 11.53 (s, 1H), 9.38 (s, 1H), 8.82 (s, 1H), 7.70 (dd, 1H, J=7.0, 1.9 Hz), 7.53 (s, 1H), 7.37 (dd, 1H, J=8.4,1.9 Hz), 6.55 (dd, 1H, J=8.2, 6.5 Hz), 2.22 (s, 3H);
$^{19}$F NMR (376 MHz, DMSO): δ −126.24 to −126.29 (m), −137.71 to −137.77 (m);
IR (KBr) 3346 (broad, O-H stretch), 1651 (C=O stretch) $cm^{-1}$;
MS (CI) M+1=484.
Analysis calculated for $C_{14}H_{10}BrF_2IN_2O_2$:
  C, 34.81; H. 2.09; N, 5.80.
Found: C, 34.53; H,. 1.73; N, 5.52,
Examples 3 to 12 in the table below were prepared by the general procedure of Examples 1a and 2a.

EXAMPLES 13a–77a

Examples 13 to 77 were prepared utilizing combinatorial synthetic methodology by reacting appropriately substituted phenylamino benzoic acids (e.g., as shown in Scheme 1) and hydroxylamines

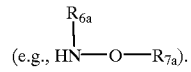

A general method is given below:
To a 0.8-niL autosampler vial in a metal block was added 40 μL of a 0.5 M solution of the acid in DMF and 40 μL of the hydroxylamine (2 M solution in Hunig's base and 1 M in amine in DMF). A 0.5 M solution of PyBrop was freshly prepared, and 50 μL were added to the autosanpler vial. The reaction was allowed to stand for 24 hours.
The reaction mixture was transferred to a 2-dram vial and diluted with 2 mL of ethyl acetate. The organic layer was washed with 3 mL of distilled water and the water layer washed again with 2 mL of ethyl acetate. The combined organic layers were allowed to evaporate to dryness in an open fume hood.
The residue was taken up in 2 mL of 50% acetonitrile in water and injected on a semi-prep reversed phase column (10 mm×25 cm, 5 μM spherical silica, pore Size 115 A derivatized with C-18, the sample was eluted at 4.7 mL/min with a linear ramp to 100% acetonitrile over 8.5 minutes. Elution with 100% acetonitrile continued for 8 minutes.) Fractions were collected by monitoring at 214 nM. The desired fractions were evaporated using a Zymark Turbovap. The product was dissolved in chloroform and transferred to a preweighed vial, evaporated, and weighed again to determine the yield. The structure was confirmed by mass spectroscopy.

EXAMPLES 3a–77a

| Example No. | Compound | Melting Point (° C.) | MS (M-H+) |
|---|---|---|---|
| 3a | 2-(4-bromo-2-methyl-phenylamino)-4-fluoro-N-hydroxy-benzamide | 56–75 dec | 523 |
| 4a | 5-Chloro-N-hydroxy-2-(4-iodo-2-methyl-phenylamino)-benzamide | 65 dec | |
| 5a | 5-Chloro-N-hydroxy-2-(4-iodo-2-methyl-phenylamino)-N-methyl-benzamide | 62–67 | |
| 6a | 5-Chloro-2-(4-iodo-2-methyl-phenylamino)-N-(terahydropyran-2-yloxy)benzamide | 105–108 | |
| 7a | 5-Chloro-2-(4-iodo-2-methyl-phenylamino)-N-methoxybenzamide | 64–68 | |
| 8a | 4-Fluoro-N-hydroxy-2-(4-fluoro-2-methyl-phenylamino)-benzamide | 119–135 | |
| 9a | 4-Fluoro-N-hydroxy-2-(2-methyl phenylamino)-benzamide | 101–103 | |
| 10a | 4-Fluoro-2-(4-fluor-2-methyl-phenylamino)-N-(terahydropyran-2-yloxy)benzamide | 142–146 | |
| 11a | 4-Fluoro-N-hydroxy-2-(4-cluoro-2-methyl-phenylamino)-benzamide | 133.5–135 | |
| 12a | 4-Fluoro-2-(4-iodo-2-methyl-phenylamino)-N-phenylmethoxy-benzamide | 107–109.5 | |
| 13a | 4-Fluoro-2-(4-iodo-2-methyl-phenylamino)-N-methoxy-benzamide | | 399 |
| 14a | 3,4-Difluoro-2-(4-iodo-2-methyl-phenylamino)-N-N-methoxy-benzamide | | 417 |
| 15a | 2-(4-Bromo-2-methyl-phenylamino)-3,4-difluoro-N-methoxy-benzamide | | 369 |
| 16a | 2-(4-Bromo-2-methyl-phenylamino)-N-ethoxy-3,4-difluoro-benzamide | | 342* (M-EtO) |
| 17a | 5-Bromo-N-ethoxy-3,4-difluoro-2-(4-iodo-2-methyl-phenylamino)-benzamide | | 509 |
| 18a | 3,4-Difluoro-2-(4-iodo-2-methyl-phenylamino)-N-isopropoxy-benzamide | | 445 |
| 19a | 2-(4-Bromo-2-methyl-phenylamino)-3,4-difluoro-N-isopropoxy-benzamide | | 397 |
| 20a | 4-Fluoro-N-(furan-3-ylmethoxy)-2-(4-iodo-2-methyl-phenylamino)-benzamide | | 465 |
| 21a | 3,4-Difluoro-N-(furan-3-ylmethoxy)-2-(4-iodo-2-methyl-phenylamino)-benzamide | | 483 |
| 22a | 2-(4-Bromo-2-methyl-phenylamino)-3,4-difluoro-N-(furan-3-ylmethoxy)-benzamide | | 435 |
| 23a | 5-Bromo-3,4-difluoro-N-(furan-3-ylmethoxy)2-(4-iodo-2-methyl-phenylamino)-benzamide | | 561 |
| 24a | 5-Bromo-N-(but-2-enyloxy)-3,4-difluoro-2-(4-iodo-2-methyl-phenylamino)-benzamide | | 536 |
| 25a | 4-Fluoro-2-(4-iodo-2-methyl-phenylamino)-N-(prop-2-ynyloxy)-benzamide | | 423 |
| 26a | 3,4-Difluoro-2-(4-iodo-2-methyl-phenylamino)-N-(prop-2-ynyloxy)-benzamide | | 441 |
| 27a | 3,4-Difluoro-2-(4-iodo-2-methyl-phenylamino)-N-(1-methyl-prop-2-ynyloxy)-benzamide | | 455 |
| 28a | 2-(4-Bromo-2-methyl-phenylamino)-3,4-difluoro-N-(1-methyl-prop-2-ynyloxy)-benzamide | | 407 |
| 29a | N-(But-3-ynyloxy)-3,4-difluoro-2-(4-iodo-2-methyl-phenylamino)-benzamide | | 455 |
| 30a | 2-(4-Bromo-2-methyl-phenylamino)-N-(but-3-ynyloxy)-3,4-difluoro-benzamide | | 407 |
| 31a | 5-Bromo-N-(but-3-ynyloxy)-3,4-difluoro-2-(4-iodo-2-methyl-phenylamino)-benzamide | | 533 |
| 32a | 3,4-Difluoro-2-(4-iodo-2-methyl-phenylamino)-N-(3-phenyl-prop-2-ynyloxy)-benzamide | | 517 |
| 33a | 3,4-Difluoro-2-(4-bromo-2-methyl-phenylamino)-N-(3-phenyl-prop-2-ynyloxy)-benzamide | | 469 |
| 34a | 3,4-Difluoro-N-[3-(3-fluoro-phenyl)-prop-2-ynyloxy]-2-(4-iodo-2-methyl-phenylamino)-benzamide | | 535 |

-continued

| Example No. | Compound | Melting Point (° C.) | MS (M-H+) |
|---|---|---|---|
| 35a | 2-(4-Bromo-2-methyl-phenylamino)-3,4-difluoro-N-[3-(3-fluoro-phenyl)-prop-2-ynyloxy]-benzamide | | 487 |
| 36a | 3,4-Difluoro-N-[3-(2-fluoro-phenyl)-prop-2-ynyloxy]-2-(4-iodo-2-methyl-phenylamino)-benzamide | | 535 |
| 37a | 5-Bromo-3,4-difluoro-N-[3-(2-fluoro-phenyl)-prop-2-ynyloxy]-2-(4-iodo-2-methyl phenylamino)-benzamide | | 613 |
| 38a | 3,4-Difluoro-2-(4-iodo-2-methyl-phenylamino)-N-(3-methyl-5-phenyl-pent-2-en-4-ynyloxy)-benzamide | | 557* *(M + H) |
| 39a | 2-(4-Bromo-2-methyl-phenylamino)-3,4-difluoro-N-(3-methyl-5-phenyl-pent-2-en-4-ynyloxy)-benzamide | | 510 |
| 40a | N-Ethoxy-3,4-difluoro-2-(4-iodo-2-methyl-phenylamino)-benzamide | | 431 |
| 41a | 2-(4-Bromo-2-methyl-phenylamino)-N-ethoxy-3,4-difluoro-benzamide | | 383 |
| 42a | 4-Fluoro-2-(4-iodo-2-methyl-phenylamino)-N-propoxy-benzamide | | 427 |
| 43a | 3,4-Difluoro-2-(4-iodo-2-methyl-phenylamino)-N-propoxy-benzamide | | 445 |
| 44a | 2-(4-Bromo-2-methyl-phenylamino)-3,4-difluoro-N-propoxy-benzamide | | 397 |
| 45a | 5-Bromo-3,4-difluoro-2-(4-iodo-2-methyl-phenylamino)-N-propoxy-benzamide | | 523 |
| 46a | 4-Fluoro-2-(4-iodo-2-methyl-phenylamino)-N-isopropoxy-benzamide | | 427 |
| 47a | 3,4-Difluoro-2-(4-iodo-2-methyl-phenylamino)-N-isopropoxy-benzamide | | 445 |
| 48a | 2-(4-Bromo-2-methyl-phenylamino)-3,4-difluoro-N-isopropoxy-benzamide | | 397 |
| 49a | 5-Bromo-3,4-difluoro-2-(4-iodo-2-methyl-phenylamino)-N-isopropoxy-benzamide | | 523 |
| 50a | N-Cyclobutyloxy-3,4-difluoro-2-(4-iodo-2-methyl-phenylamino)-benzamide | | 457 |
| 51a | 2-(4-Bromo-2-methyl-phenylamino)-N-cyclobutyloxy-3,4-difluoro-benzamide | | 409 |
| 52a | N-Cyclopentyloxy-4-fluoro-2-(4-iodo-2-methyl-phenylamino)-benzamide | | 453 |
| 53a | N-Cyclopentyloxy-3,4-difluoro-2-(4-iodo-2-methyl-phenylamino)-benzamide | | 471 |
| 54a | 2-(4-Bromo-2-methyl-phenylamino)-N-cyclopentyloxy-3,4-difluoro-benzamide | | 423 |
| 55a | N-Cyclopropylmethoxy-4-fluoro-2-(4-iodo-2-methyl-phenylamino)-benzamide | | 439 |
| 56a | N-Cyclopropylmethoxy-3,4-difluoro-2-(4-iodo-2-methyl-phenylamino)-benzamide | | 457 |
| 57a | 2-(4-Bromo-2-methyl-phenylamino)-N-cyclopropylmethoxy-3,4-difluoro-benzamide | | 409 |
| 58a | 5-Bromo-N-cyclopropylmethoxy-3,4-difluoro-2-(4-iodo-2-methyl-phenylamino) | | 435 |
| 59a | 4-Fluoro-2-(4-iodo-2-methyl-phenylamino)-N-(2-phenoxy-ethoxy)-benzamide | | 505 |
| 60a | 3,4-Difluoro-2-(4-iodo-2-methyl-phenylamino)-N-(2-phenoxy-ethoxy)-benzamide | | 523 |
| 61a | 2-(4-Bromo-2-methyl-phenylamino)-3,4-difluoro-N-(2-phenoxy-ethoxy)-benzamide | | 475 |
| 62a | 4-Fluoro-2-(4-iodo-2-methyl-phenylamino)-N-(thiophen-2-ylmethoxy)-benzamide | | 481 |
| 63a | 3,4-Difluoro-2-(4-iodo-2-methyl-phenylamino)-N-(thiophen-2-ylmethoxy)-benzamide | | 499 |
| 64a | 2-(4-Bromo-2-methyl-phenylamino)-3,4-difluoro-N-(thiophen-2-ylmethoxy)-benzamide | | 451 |
| 65a | 4-Fluoro-2-(4-iodo-2-methyl-phenylamino)-N-(2-methyl-allyloxy)-benzamide | | 439 |
| 66a | 3,4-Difluoro-2-(4-iodo-2-methyl-phenylamino)-N-(2-methyl-allyloxy)-benzamide | | 457 |
| 67a | 2-(4-Bromo-2-methyl-phenylamino)-3,4-difluoro-N-(2-methyl-allyloxy)-benzamide | | 410 |
| 68a | N-(But-2-enyloxy)-4-fluoro-2-(4-iodo-2-methyl-phenylamino)-benzamide | | 439 |
| 69a | N-(But-2-enyloxy)-3,4-difluoro-2-(4-iodo-2-methyl-phenylamino)-benzamide | | 457 |

-continued

| Example No. | Compound | Melting Point (° C.) | MS (M-H⁺) |
|---|---|---|---|
| 70a | 2-(4-Bromo-2-methyl-phenylamino)-N-(but-2-enyloxy)-3,4-difluoro-benzamide | | 410 |
| 71a | 3,4-Difluoro-2-(4-iodo-2-methyl-phenylamino)-N-(prop-2-ynyloxy)-benzamide | | 441 |
| 72a | N-(But-3-ynyloxy)-3,4-difluoro-2-(4-iodo-2-methyl-phenylamino)-benzamide | | 455 |
| 73a | 2-(4-Bromo-2-methyl-phenylamino)-N-(4,4-dimethyl-pent-2-ynyloxy)-3,4-difluoro-benzamide | | 449 |
| 74a | N-(But-2-enyloxy)-3,4-difluoro-2-(4-iodo-2-methyl-phenylamino)-benzamide | | 457 |
| 75a | 2-(4-Bromo-2-methyl-phenylamino)-N-(but-2-enyloxy)-3,4-difluoro-benzamide | | 410 |
| 76a | N-(3-tert.-butyl-propyn-2-yl)oxy-4-fluoro-2-(4-iodo-2-methyl-phenylamino)-benzamide | | 479 |
| 77a | 4-Fluoro-2-(4-iodo-2-methyl-phenylamino)-N-phenylmethoxy-benzamide | | 577* *Cl |

Enzyme Assays

Cascade assay for inhibitors of the MAP kinase pathway

Incorporation of $^{32}P$ into myelin basic protein (MBP) was assayed in the presence of a glutathione S-transferase fusion protein containing p44MAP kinase (GST-MAPK) and a glutathione S-transferase fusion protein containing p45MEK (GST-MEK). The assay solution contained 20 mM HEPES, pH 7.4, 10 MM $MgCl_2$, 1 mM $MnCl_2$, 1 mM EGTA, 50 µM [γ-$^{32}$P]ATP, 10 µg GST-MEK, 0.5 µg GST-MAPK and 40 µg MBP in a final volume of 100 µL. Reactions were stopped after 20 minutes by addition of trichloroacetic acid and filtered through a GF/C filter mat. $^{32}P$ retained on the filter mat was determined using a 1205 Betaplate. Compounds were assessed at 10 µM for ability to inhibit incorporation of $^{32}P$.

To ascertain whether compounds were inhibiting GST-MEK or GST MAPK, two additional protocols were employed. In the first protocol, compounds were added to tubes containing GST-MEK, followed by addition of GST-MAPK, MBP and [γ-$^{32}$P]ATP. In the second protocol, compounds were added to tubes containing both GST-MEK and GST-MAPK, followed by MBP and [γ-$^{32}$P]ATP. Compounds that showed activity in both protocols were scored as MAPK inhibitors, while compounds showing activity in only the first protocol were scored as MEK inhibitors.

In vitro MAP kinase assay

Inhibitory activity was also confirmed in direct assays. For MAP kinase, 1 µg GST-MAPK was incubated with 40 µg MBP for 15 minutes at 30° C. in a final volume of 50 µL containing 50 mM Tris (pH 7.5), 10 µM $MgCl_2$, 2 µM EGTA, and 10 µM [γ-$^{32}$P]ATP. The reaction was stopped by addition of Laemmli SDS sample buffer and phosphorylated MBP resolved by electrophoresis on a 10% polyacrylamide gel. Radioactivity incorporated into MBP was determined by autoradiography, and subsequently by excision of the bands followed by scintillation counting.

In vitro MEK assay

For evaluation of direct MEK activity, 10 µg GST-MEK₁ was incubated with 5 µg of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations were 15 minutes at 30° C in a final volume of 50 µL containing 50 mM Tris (pH 7.5), 10 µM $MgCl_2$, 2 µM EGTA, and 10 µM [γ-$^{32}$P]ATP. The reaction was stopped by addition of Laemnuli SDS sample buffer and phosphorylated GST-MAPK-KA was resolved by electrophoresis on a 10% polyacrylamide gel. Radioactivity incorporated into GST-MAPK-KA was determined by autoradiography, and subsequently by excision of the bands followed by scintillation counting. Additionally, an artificially activated MEK was utilized that contained serine to glutamate mutations at positions 218 and 222 (GST-MEK-2E). When these sites are phosphorylated, MEK activity is increased. Phosphorylation of these sites can be mimicked by mutation of the serine residues to glutamate. For this assay, 5 µg GST-MEK-2E was incubated with 5 µg GST-MAPK-KA for 15 minutes at 30° C. in the same reaction buffer as described above. Reactions were terminated and analyzed as above.

Whole cell MAP kinase assay

To determine if compounds were able to block activation of MAP kinase in whole cells, the following protocol was used: Cells were plated in multi-well plates and grown to confluence. Cells were then serum-deprived overnight. Cells were exposed to the desired concentrations of compound or vehicle (DMSO) for 30 minutes, followed by addition of a growth factor, for example, PDGF (100 ng/mL). After a 5-minute treatment with the growth factor, cells were washed with PBS, then lysed in a buffer consisting of 70 mM NaCl, 10 mM HEPES (pH 7.4), 50 mM glycerol phosphate, and 1% Triton X-100. Lysates were clarified by centrifugation at 13,000×g for 10 minutes. Five micrograms of the resulting supernatants were incubated with 10 jig microtubule associated protein-2 (Map2) for 15 minutes at 30° C. in a final volume of 25 µL containing 50 mM Tris (pH 7.4), 10 mM $MgCl_2$, 2 mM EGTA and 30 µM [γ-$^{32}$P]ATP. Reactions were terminated by addition of Laemmli sample buffer. Phosphorylated Map2 was resolved on 7.5% acrylamide gels and incorporated radioactivity determined by autoradiography and subsequent excision of the bands followed by scintillation counting.

Immunoprecipitation and antiphosphotyrosine immunoblots

To determine the state of tyrosine phosphorylation of cellular MAP kinase, cells were lysed, endogenous MAP kinase was immunoprecipitated with a specific antibody, and the resulting inmmunoprecipitate analyzed for the presence of phosphotyrosine as follows: confluent cells were serum-deprived overnight and treated with compounds and growth factors as described above. Cells were then scraped and pelleted at 13,000×g for 2 minutes. The resulting cell pellet was resuspended and dissolved in 100 μL of 1% SDS containing 1 mM $NaVO_4$. Following alternate boiling and vortexing to denature cellular protein, 900 μL RIPA buffer (50 mM Tris (pH 7.4), 150 mM NaCl, 1% Triton X-100, 0.1% deoxycholate, and 10 mM EDTA) was added. To this mixture was added 60 μL agarose beads coupled with rabbit immunoglobulin G and 60 μL Pansorbin cells in order to clear the lysate of nonspecific binding proteins. This mixture was incubated at 4° C. for 15 minutes then centrifuged at 13,000×g for 10 minutes. The resulting supernatant was transferred to fresh tubes and incubated with 10 μL of a polyclonal antisera raised against a fragment of MAP kinase for a minimum of 1 hour at 4° C. Seventy microliters of a slurry of agarose beads coupled with protein G and protein A was added and the incubation continued for an additional 30 minutes at 4° C. The beads were pelleted by centrifugation at 13,000×g for 5 minutes and washed three times with 1 mL RIPA buffer. Laemmli sample buffer was added to the final bead pellet. This mixture was boiled for 5 minutes then resolved on a 10% acrylamide gel. Proteins on the gel were transferred to a nitrocellulose membrane and nonspecific binding sites on the membrane blocked by incubation with 1% ovalbumin and 1% bovine serum albumin in TBST (150 mM NaCl, 10 mM Tris (pH 7.4), and 0.05% Tween 20). The membrane was then incubated with a commercially available antibody directed against phosphotyrosine. Antibody bound on the membrane was detected by incubation with $^{125}$I-protein A, followed by autoradiography.

Cell Growth Assays

$^3$H-Thymidine incorporation

Cells were plated in multi-well plates and grown to near confluence. The media was then removed and replaced with growth media containing 1% bovine serum albumin. After 24-hour serum starvation, compounds and specific growth factors were added and incubations continued for an additional 24 hours. During the final 2 hours, $^3$H-thymidine was added to the medium. To terminate the incubations, the medium was removed and cell layers washed twice with ice-cold phosphate-buffered saline. After the final wash, ice-cold 5% trichloroacetic acid was added and the cells incubated for 15 minutes at room temperature. The trichloroacetic acid solution was then removed and the cell layer washed three times with distilled water. After the final wash, the cell layer was solubilized by addition of 2% sodium dodecylsulfate. Radioactivity in this solution was determined by scintillation counting.

In 3T3-L1 adipocyte cells, in which the inhibition blocks MAPK activation by insulin with an $IC_{50}$ of 3 μM, the compound had no effect on the insulin stimulated uptake of radiolabeled 2-deoxyglucose, or on the insulin-stimulated synthesis of either lipid or glycogen at 10 μM concentration. This demonstrates that the inhibitor shows selectivity between the mitogenic and metabolic effects of insulin, and demonstrates that the inhibitor will show less toxicity than an inhibitor which does not show this surprising selectivity.

Monolayer growth

Cells were plated into multi-well plates at 10 to 20,000 cells/mL. Forty-eight hours after seeding, compounds were added to the cell growth medium and incubation was continued for 2 additional days. Cells were then removed from the wells by incubation with trypsin and enumerated with a Coulter counter.

Growth in soft-agar

Cells were seeded into 35-mm dishes at 5 to 10,000 cells/dish using growth medium containing 0.3% agar. After chilling to solidify the agar, cells were transferred to a 37° C. incubator. After 7 to 10 days growth, visible colonies were manually enumerated with the aid of a dissecting microscope.

Order of addition experiments established that the invention compounds are inhibiting MEK and not MAP kinase. Experiments looking at the phosphorylation of a kinase defective mutant of MAP kinase as substrate (so that there can be no autophosphorylation of the MAP kinase to complicate interpretation) confirms that the inhibitor inhibits MEK with an $IC_{50}$ essentially identical to that produced in the cascade assay.

Kinetic analysis demonstrates that the invention compounds are not competitive with ATP. Thus, they do not bind at the ATP binding site of the enzyme, which is probably the explanation as to why these compounds do not show the nonspecific kinase inhibitory activity typical of most kinase inhibitors, which do not bind at the ATP binding site and which are ATP competitive.

The in vitro and in vivo biological activity of several representative compounds of Formula I and II in the foregoing assays is presented in Tables 1 and 2.

TABLE 1

| Compound of Example No. | In Vitro % Inhibition | In Vitro $IC_{50}$ μM | In Vivo % Inhibition | In Vivo $IC_{50}$ μM |
|---|---|---|---|---|
| 4 |  | 0.005 |  | 1 |
| 3 |  | 0.0111 |  | 10 |
| 2 |  | 0.014 |  | 3 |
| 1 |  | 0.019 |  |  |
| 32 |  | 0.028 |  |  |
| 53 |  | 0.047 |  | 0.54 |
| 33 |  | 0.052 |  |  |
| 5 |  | 0.066 |  |  |
| 6 |  | 0.071 |  |  |
| 7 |  | 0.072 |  |  |
| 8 |  | 0.086 |  |  |
| 9 |  | 0.097 |  |  |
| 34 |  | 0.098 |  |  |
| 10 |  | 0.101 |  |  |
| 55 |  | 0.114 |  |  |
| 35 |  | 0.121 |  |  |
| 11 |  | 0.128 |  |  |
| 36 |  | 0.129 |  |  |
| 12 |  | 0.135 |  |  |
| 54 |  | 0.158 |  |  |
| 13 |  | 0.178 |  |  |
| 14 |  | 0.179 |  |  |
| 15 |  | 0.194 |  |  |
| 31 |  | 0.226 |  |  |
| 37 |  | 0.237 |  |  |
| 92 |  | 0.253 |  |  |
| 184 |  | 0.278 |  |  |
| 16 |  | 0.323 |  |  |
| 96 |  | 0.374 |  |  |
| 57 |  | 0.399 |  |  |
| 38 |  | 0.412 |  |  |
| 49 |  | 0.418 |  | 3 |
| 17 |  | 0.434 |  |  |
| 18 |  | 0.446 |  |  |
| 91 |  | 0.449 |  |  |
| 39 |  | 0.497 |  |  |

TABLE 1-continued

| Compound of Example No. | In Vitro % Inhibition | In Vitro IC$_{50}$ μM | In Vivo % Inhibition | In Vivo IC$_{50}$ μM |
|---|---|---|---|---|
| 93 | | 0.521 | | |
| 19 | | 0.524 | 50% at 30 μM | |
| 186 | | 0.555 | | |
| 20 | | 0.557 | | |
| 187 | | 0.561 | | |
| 21 | | 0.569 | | |
| 90 | | 0.604 | | |
| 89 | | 0.614 | | |
| 40 | | 0.651 | 30% at 30 μM | |
| 188 | | 0.771 | | |
| 189 | | 0.859 | | |
| 41 | | 0.872 | | |
| 51 | | 0.887 | | |
| 42 | | 0.920 | | |
| 190 | | 0.921 | | |
| 43 | | >1.000 | | |
| 95 | | 1.001 | | |
| 208 | | 1.215 | | |
| 191 | | 1.355 | | |
| 209 | | 1.372 | | |
| 44 | | 1.481 | | |
| 22 | | 1.581 | 30% at 30 μM | |
| 23 | | 1.588 | | |
| 45 | | 1.755 | | |
| 192 | | 1.797 | | |
| 46 | | 1.814 | | |
| 47 | | 1.911 | | |
| 24 | | 1.944 | | |
| 48 | | 1.945 | | |
| 100 | | 1.994 | | |
| 91 | | 2.071 | | |
| 27 | | 2.269 | | |
| 52 | | 2.346 | | |
| 25 | | 2.363 | | |
| 26 | | 2.609 | 50% at 30 μM | |
| 193 | | 2.902 | | |
| 28 | | 3.670 | | |
| 194 | | 4.952 | | |
| 29 | | 5.331 | | |
| 195 | | 12.831 | | |
| 30 | | 105 | | 10 |

TABLE 2

| Compound of Example No. | In vitro IC$_{50}$ (μM) | In vivo IC$_{50}$ (μM) |
|---|---|---|
| 1a | 0.007 | 0.05 |
| 2a | 0.003 | 0.03 |
| 3a | 0.072 | 3 |
| 4a | 0.023 | 1 |
| 5a | 0.566 | ~30 |
| 6a | 0.345 | ~30 |
| 7a | 0.221 | <30 |
| 8a | 7.13 | 3 |
| 9a | 0.409 | 1 |
| 11a | 0.334 | 0.5 |
| 12a | 0.826 | |
| 13a | 0.243 | |
| 14a | 0.061 | >2 |
| 17a | 0.014 | |
| 20a | 0.042 | 0.17 |
| 21a | 0.014 | |
| 22a | 0.137 | |
| 23a | 0.016 | |
| 24a | 0.021 | 0.12 |
| 25a | 0.102 | |
| 27a | 0.026 | |
| 28a | 0.728 | |
| 29a | 0.076 | 0.73 |
| 30a | 0.971 | |
| 31a | 0.045 | |
| 32a | 0.017 | |
| 33a | 0.374 | |
| 34a | 0.113 | 1.5 |
| 36a | 0.056 | 0.07 |
| 40a | 0.028 | 0.125 |
| 41a | 0.236 | |
| 42a | 0.087 | |
| 43a | 0.040 | 0.100 |
| 44a | 0.475 | |
| 45a | 0.126 | |
| 47a | 0.087 | 0.13 |
| 49a | 0.085 | |
| 50a | 0.043 | 0.22 |
| 53a | 0.140 | |
| 55a | 0.047 | |
| 56a | 0.014 | |
| 57a | 0.181 | |
| 58a | 0.018 | 0.014 |
| 59a | 0.259 | |
| 62a | 0.086 | |
| 63a | 0.019 | |
| 64a | 0.279 | |
| 65a | 0.057 | |
| 66a | 0.016 | 0.13 |
| 68a | 0.119 | |
| 69a | 0.016 | |
| 70a | 0.224 | |
| 71a | 0.015 | 0.39 |
| 74a | 0.035 | |
| 77a | 0.28 | |

What is claimed is:

1. A method of treating or prophylactic treatment of patients at risk to suffer from septic shock, the method comprising administering to a patient having septic shock or at risk of having septic shock a therapeutically acceptable amount of a compound that is a MEK inhibitor.

2. The method of claim 1 wherein the compound is 2-(2-amino-3-methoxyphenyl)-4-oxo-4H-[1]benzopyran.

3. The method of claim 1 wherein the patient has septic shock.

4. The method of claim 1 wherein the patient is at risk of having septic shock.

5. A method of treating or prophylactic treatment of patients at risk to suffer from septic shock, the method comprising administering to a patient having septic shock or at risk of having septic shock a therapeutically acceptable amount of 2-(2-amino-3-methoxyphenyl)-4-oxo4H-[1]benzopyran.

6. The method of claim 1 wherein the MEK inhibitor is a compound of Formula I

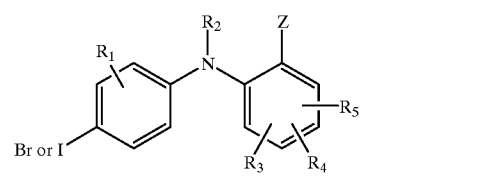

wherein:
R$_1$ is hydrogen, hydroxy, C$_1$–C$_8$ alkyl, C$_1$–C$_8$ alkoxy, halo, trifluoromethyl, or CN;
R$_2$ is hydrogen;
R$_3$, R$_4$, and R$_5$ independently are hydrogen, hydroxy, halo, trifluoromethyl, C$_1$–C$_8$ alkyl, C$_1$–C$_8$ alkoxy, nitro, CN, or —(O or NH)$_m$—(CH$_2$)$_n$—R$_9$, where R$_9$ is hydrogen, hydroxy, COOH, or NR$_{10}$R$_{11}$;

n is 0–4;

m is 0 or 1;

$R_{10}$ and $R_{11}$ independently are hydrogen or $C_1$–$C_8$ alkyl, or taken together with the nitrogen to which they are attached can complete a 3–10 member cyclic ring optionally containing 1, 2, or 3 additional heteroatoms selected from O, S, NH, or N—$C_1$–$C_8$ alkyl;

Z is $COOR_7$, tetrazolyl, $CONR_6R_7$, $CONHNR_{10}R_{11}$, or $CH_2OR_7$;

$R_6$ and $R_7$ independently are hydrogen, $C_1$–$C_8$ alkyl, $C_2$–$C_8$ alkenyl, $C_2$–$C_8$ alkynyl,

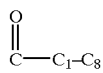

alkyl, aryl, heteroaryl, $C_3$–$C_{10}$ cycloalkyl, or $C_3$–$C_{10}$ (cycloalkyl optionally containing one, two, or three heteroatoms selected from O, S, NH, or N alkyl); or $R_6$ and $R_7$ together with the nitrogen to which they are attached complete a 3–10 member cyclic ring optionally containing 1, 2, or 3 additional heteroatoms selected from O, S, NH, or N alkyl;

and wherein any of the foregoing alkyl, alkenyl, and alkynyl groups can be unsubstituted or substituted by halo, hydroxy, alkoxy, amino, alkylamino, dialkylamino, cycloalkyl, aryl, aryloxy, heteroaryl, or heteroaryloxy, and the pharmaceutically acceptable salts, esters, amides, or prodrugs thereof.

7. The method of claim 6 wherein the MEK inhibitor is

[4-Chloro-2-(1H-tetrazol-5-yl)-(4-iodo-2-methyl-phenyl)-amine;

(4-iodo-2-methyl-phenyl)-[2-(1H-tetrazol-5-yl)-phenyl] amine;

[4-nitro-2-(1H-tetrazol-5-yl)-(4-iodo-2-methyl-phenyl)-amine;

4-Fluoro-2-(4-iodo-2-methylphenylamino)benzoic acid;

3,4,5-Trifluoro-2-(4-iodo-2-methyl-phenylamino)-benzoic acid;

3,4-Difluoro-2-(4-iodo-2-methyl-phenylamino)-benzoic acid;

5-Bromo-3,4-difluoro-2-(4-iodo-2-methyl-phenylamino)-benzoic acid;

5-Chloro-2-(4-iodo-2-methyl-phenylamino)-benzoic acid;

Sodium 5-Chloro-2-(4-iodo-2-methyl-phenylamino)-benzoate;

5-Bromo-2-(4-iodo-2-methyl-phenylamino)-benzoic acid;

2-(4-Iodo-2-methyl-phenylamino)-5-nitro-benzoic acid;

4-Chloro-2-(4-iodo-2-methyl-phenylamino)-benzoic acid;

2-(4-Iodo-2-methyl-phenylamino)-benzoic acid;

5-Fluoro-2-(4-iodo-2-methyl-phenylamino)-benzoic acid;

5-Iodo-2-(4-iodo-2-methyl-phenylamino)-benzoic acid;

2,3,5-Trifluoro-4-(4-iodo-2-methyl-phenylamino)-benzoic acid;

2-(4-Iodo-phenylamino)-5-methoxy-benzoic acid;

5-Methyl-2-(4-iodo-2-methyl-phenylamino)-benzoic acid;

2-(4-Iodo-2-methyl-phenylamino)-4-nitro-benzoic acid;

2-(4-Brom-2-methyl-phenylmnino)-4-fluoro-benzoic acid;

2-(2-Bromo-4-iodo-phenylamino)-5-nitro-benzoic acid;

2-(4-Bromo-2-methyl-phenylamino)-3,4-difluoro-benzoic acid;

5-Chloro-N-(2-hydroxyethyl)-2-(4-iodo-2-methyl-phenylamino)-benzamide;

4-Fluoro-2-(4-iodo-2-methyl-phenylamino)-benzamide;

4-Fluoro-2-(4-iodo-2-methyl-phenylamino)-N-methyl-benzamide;

N-Ethyl-4-fluoro-2-(4-iodo-2-methyl-phenylamino)-benzamide;

4-Fluoro-2-(4-iodo-2-methyl-phenylamino)-N,N-dimethyl-benzamide;

4-Fluoro-2-(4-iodo-2-methyl-phenylamino)-N-(1H-tetrazol-5-yl)-benzamide;

5-Bromo-2-(4-iodo-2-methyl-phenylamino)-benzamide;

5-Chloro-2-(4-iodo-2-methyl-phenylamino)-N,N-dimethyl-benzamide;

[5-Chloro-2-(4-iodo-2-methyl-phenylamino)-benzoylamino]-acetic acid;

4-Fluoro-2-(4-iodo-2-methyl-phenylamino)-N-propyl-benzamide;

5-Bromo-N-(2-hydroxy-ethyl)-2-(4-iodo-2-methyl-phenylamino)-benzamide;

N,N-Diethyl-4-fluoro-2-(4-iodo-2-methyl-phenylamino)-benzamide;

4-Fluoro-N-{3-[4-(2-hydroxy-ethyl)-piperazin-1-yl]-propyl}-2-(4-iodo-2-methyl-phenylamino)-benzamide;

N,N-Diethyl-2-(4-iodo-2-methyl-phenylamino)-5-nitro-benzamide;

N-Butyl-4-fluoro-2-(4-iodo-2-methyl-phenylamino)-benzamide;

5-Chloro-N,N-diethyl-2-(4-iodo-2-methyl-phenylamino)-benzamide;

5-Bromo-2-(4-iodo-2-methyl-phenylamino)-N,N-dimethyl-benzamide;

5-Bromo-3,4-difluoro-N-(2-hydroxy-ethyl)-2-(4-iodo-2-methyl-phenylamino)-benzamide;

N-(2,3-Dihydroxy-propyl)-3,4-difluoro-2-(4-iodo-2-methyl-phenylamino)-benzamide;

5-Bromo-3,4difluoro-2-(4-iodo-2-methyl-phenylamino)-N-(2-piperidin-1-yl-ethyl)-benzamide;

3,4-Difluoro-N-(2-hydroxy-ethyl)-2-(4-iodo-2-methyl-phenylamino)-benzamide;

N-(2,3-Dihydroxy-propyl)-4-fluoro-2-(4-iodo-2-methyl-phenylamino)-benzamide;

3,4-Difluoro-N-(3-hydroxy-propyl)-2-(4-iodo-2-methyl-phenylamino)-benzamide;

5-Bromo-3,4-difluoro-2-(4-iodo-2-methyl-phenylamino)-N-(2-pyrrolidin-1-yl-ethyl)-benzamide;

5-Bromo-3,4-difluoro-2-(4-iodo-2-methyl-phenylamino)-N-(2-pyridin4-yl-ethyl)-benzamide;

4-Fluoro-N-(2-hydroxy-ethyl)-2-(4-iodo-2-methyl-phenylamino)-benzamide;

5-Bromo-N-(3-dimethylamino-propyl)-3,4-difluoro-2-(4-iodo-2-methyl-phenylamino)-benzamide;

5-Bromo-3,4-difluoro-2-(4-iodo-2-methyl-phenylamino)-N-(2-morpholin4-yl-ethyl)-benzamide;

3,4-Difluoro-2-(4-iodo-2-methyl-phenylamino)-N-(2-morpholin-4-yl-ethyl)-benzamide;

3,4-Difluoro-2-(4-iodo-2-methyl-phenylamino)-N-(2-pyrrolidin-1-yl-ethyl)-benzamide;
3,4-Difluoro-2-(4-iodo-2-methyl-phenylamino)-N-(2-pyridin-4-yl-ethyl)-benzamide;
N-(3-Dimethylamino-propyl)-3,4-difluoro-2-(4-iodo-2-methyl-phenylamino)-benzamide;
N-Benzyl4-fluoro-2-(4-iodo-2-methyl-phenylamino)-benzamide;
2-(4-Bromo-2-methyl-phenylamino)-3,4-difluoro-N-(2-hydroxy-ethyl)-benzamide;
4-Fluoro-2-(4-iodo-2-methyl-phenylamino)-N-(2-morpholin4-yl-ethyl)-benzamide;
4-Fluoro-2-(4-iodo-2-methyl-phenylamino)-N-(3-piperidin-1-yl-propyl)-benzamide;
3,4-Difluoro-2-(4-iodo-2-methyl-phenylamino)-N-(3-piperidin-1-yl-propyl)-benzamide;
4-Fluoro2-(4-iodo-2-methyl-phenylamino)-N-(2-thiophen-2-yl-ethyl)-benzamide;
4-Fluoro-2-(4-iodo-2-methyl-phenylamino)-N-(2-pyrrolidin-1-yl-ethyl)-benzamide;
2-(4-Bromo-2-methyl-phenylamino)-3,4-difluoro-N-(2-morpholin-4-yl-ethyl)-benzamide;
5-Bromo-3,4-difluoro-2-(4-iodo-2-methyl-phenylamino)-N-pyridin-4-yl-methyl-benzamide;
3,4-Difluoro-2-(4-iodo-2-methyl-phenylamino)-N-pyridin-4-ylmethyl-benzamide;
2-(4-Bromo-2-methyl-phenylamino)-N-(3-dimethylamino-propyl)-3,4-difluoro-benzamide;
4-Fluoro-2(44-iodo-2-methyl-phenylamino)-N-pyridin-4-ylmethyl-benzamide;
4-Fluoro-2-(4-iodo-2-methyl-phenylamino)-N-(2-pyridin4-yl-ethyl)-benzamide;
2-(4-Bromo-2-methyl-phenylamino)-3,4-difluoro-N-(2-pyridin-4-yl-ethyl)-benzamide;
2-(4-Bromo-2-methyl-phenylamino)-3,4-difluoro-N-(3-hydroxy-propyl)-benzamide;
2-(4-Bromo-2-methyl-phenylamino)-3,4-difluoro-N-(2-pyrrolidin-1-yl-ethyl)-benzamide;
4-Fluoro-2-(4-iodo-2-methyl-phenylamino)-N-phenethyl-benzamide;
2-(4-Bromo-2-methyl-phenylamino)-3,4-difluoro-N-(2-thiophen-2-yi-ethyl)-benzamide;
2-(4-Bromo-2-methyl-phenylamino)-3,4-difluoro-N-pyridin-4-ylmethyl-benzamide;
2-(4-Bromo-2-methyl-phenylamino)-3,4-difluoro-N-phenethyl-benzamide;
2-(4-Bromo-2-methyl-phenylamino)-3 ,4-difluoro-N-(2-piperidin-1-yl-ethyl)-benzamide;
5-Chloro-N-{3-[4-(2-hydroxy-ethyl)-piperazin-1-yl]-propyl}-2-(4-iodo-2-methyl-phenylamino)-benzamide;
5-Fluoro-N-{3-[4-(2-hydroxy-ethyl)-piperazin-1-yl]-propyl}-2-(4-iodo-2-methyl-phenylamino)-benzamide;
2-(4-Iodo-2-methyl-phenylamino)-5-nitro-N-pyridin-4-yl methyl-benzamide;
5-Bromo-N-{3-[4-(2-hydroxy-ethyl)-piperazin-1-yl]-propyl}-2-(4-iodo-2-methyl-phenylamino)-benzamide;
5-Chloro-N-(2-diethylamino-ethyl)-2-(4-iodo-2-methyl-phenylamino)-benzamide;
5-Chloro-2-(4-iodo-2-methyl-phenylamino)-N-(2-piperidin-1-yl-ethyl)-benzamide;
(3-Hydroxy-pyrrolidin-1-yl)-[2-(4-iodo-2-methyl-phenylamino)-5-nitro-phenyl];
5-Chloro-2-(4-iodo-2-methyl-phenylamino)-N-(2-pyrrolidin-1 -yl-ethyl)-benzamide;
5-Bromo-N-(2-diethylamino-ethyl)-2-(4-iodo-2-methyl-phenylamino)-benzamide;
N-{2-[Bis-(2-hydroxy-ethyl)amino]-ethyl}-5-chloro-2-(4-iodo-2-methyl-phenylamino)-benzamide;
N-{2-[Bis-(2-hydroxy-ethyl)-amino]-ethyl}-5-bromo-2-(4-iodo-2-methyl-phenylamino)-benzamide;
N-{3-[4-(2-Hydroxy-ethyl)-piperazin-1-yl]-propyl}-2-(4-iodo-2-methyl-phenylamino)- benzamide;
5-Fluoro-2-(4-iodo-2-methyl-phenylamino)-N-pyridin-4-ylmethyl-benzamide;
5-Bromo-2-(4-iodo-2-ethyl-phenylamino)-N-(2-pyrrolidin-1-yl-ethyl)-benzamide;
5-Bromo-2-(4-iodo-2-methyl-phenylamino)-N-(2-piperidin-1-yl-ethyl)-benzamide;
5-Fluoro-2-(4-iodo-2-methyl-phenylamino)-N-(2-pyrrolidin-1-yl-ethyl)-benzamide;
5-Chloro-N-(3-dimethylamino-propyl)-2-(4-iodo-2-methyl-phenylamino)-benzamide;
N-{2-[Bis-(2-hydroxy-ethyl)-amino]-ethyl}-5-fluoro-2-(4-iodo-2-methyl-phenylamino)-benzamide;
5-Chloro-N-(3-hydroxy-propyl)-2-(4-iodo-2-methyl-phenylamino)-benzamide;
5-Chloro-N-(3-diethylanino-2-hydroxy-propyl)-2-(4-iodo-2-methyl-phenylamino)-benzamide;
5-Fluoro-2-(4-iodo-2-methyl-phenylamino)-N-(2-piperidin-1-yl-ethyl)-benzamide;
5-Bromo-N-(3-hydroxy-propyl)-2-(4-iodo-2-methyl-phenylamino)-benzamide;
5-Bromo-2-(4-iodo-2-methyl-phenylamino)-N-(3-piperidin-1-yl-propyl)-benzamide;
N-{2-[Bis-(2-hydroxy-ethyl)-amino]-ethyl}-2-(4-iodo-2-methyl-phenylamino)-5-nitro-benzamide;
5-Chloro-2-(4-iodo-2-methyl-phenylamino)-N-(2-morpholin-4-yl-ethyl)-benzamide;
5-Chloro-N-3-diethylamino-propyl)-2-(4-iodo-2-methyl-phenylamino)-benzamide;
5-Chloro-N-(2-diisopropylamino-ethyl)-2-(4-iodo-2-methyl-phenylamino)-benzamide;
5-Chloro-2-(4-iodo-2-methyl-phenylamino)-N-(3-piperidin-1-yl-propyl)-benzamide;
2-(4-Iodo-2-methyl-phenylamino)-5-nitro-N-(2-piperidin-1-yl-ethyl)-benzamide;
5-Bromo-2-(4-iodo-2-methyl-phenylamino)-N-(2-piperazin-1-yl-ethyl)-benzamide;
N-(2-Diethylamino-ethyl)-5-fluoro-2-(4-iodo-2-methyl-phenylamino)-benzamide;
5-Bromo-N-(3-dimethylamino-propyl)-2-(4-iodo-2-methyl-phenylamino)-benzamide;
N-(3-Hydroxy-propyl)-2-(4-iodo-2-methyl-phenylamino)-5-nitro-benzamide;
5-Fluoro-N-(3-hydroxy-propyl)-2-4-iodo-2-methyl-phenylamino)-benzamide;
N-(3-Diethylamino-propyl)-5-fluoro-2-(4-iodo-2-methyl-phenylamino)-benzamide;
N-(3-Diethylamino-propyl)-2-(4-iodo-2-methyl-phenylamino)-5-nitro-benzamide;
5-Bromo-2-(4-iodo-2-methyl-phenylamino)-N-(2-morpholin-4-yl-ethyl)-benzamide;
2-(4-Iodo-2-methyl-phenylamino)-5-nitro-N-(3-piperidin-1-yl-propyl)-benzamide;

[5-Fluoro-2-(4-iodo-2-methyl-phenylamino)-phenyl]-(3-hydroxy-pyrrolidin-1-yl)-;

5-Bromo-N-(2-diisopropylamino-ethyl)-2-(4-iodo-2-methyl-phenylamino)-benzamide;

5-Fluoro-2-(4-iodo-2-methyl-phenylamino)-N-(2-morpholin-4-yl-ethyl)-benzamide;

5-Fluoro-2-(4-iodo-2-inethyl-phenylamino)-N-(3-piperidin-1-yl-propyl)-benzamide;

[5-Fluoro-2-(4iodo-2-methyl-phenylamino)-phenyl]-[4-(2-hydroxy-ethyl)-piperazin-1-;

N-(3-Diethylamino-2-hydroxy-propyl)-5-fluoro-2-(4-iodo-2-methyl-phenylamino)-benzamide;

N-Cyclopropyl-5-fluoro-2-(4-iodo-2-methyl-phenylamino)-benzamide;

5-Chloro-N-(2-hydroxy-ethyl)-2-(4-iodo-2-methyl-phenylamino)-benzamide;

5-Fluoro-N-(2-hydroxy-ethyl)-2-(4-iodo-2-methyl-phenylamino)-benzamide;

N-Benzyloxy-5-fluoro-2-(4iodo-2-methyl-phenylamino)-benzamide;

N-Benzyloxy-5-bromo-2-(4-iodo-2-methyl-phenylamino)-benzamide;

2-(4-Iodo-2-methyl-phenylamino)-5-nitro-N-(4-sulfamoyl-benzyl)-benzamide;

5-Bromo-N-(2-hydroxy-ethyl)-2-(4-iodo-2-methyl-phenylamino)-benzamide;

N-(2-Hydroxy-ethyl)-5-iodo-2-(4-iodo-2-methyl-phenylamino)-benzamide;

N-(2-Hydroxy-ethyl)-2-(4-iodo-2-ethyl-phenylamino)-5-nitro-benzamide;

2-(4-Iodo-2-methyl-phenylamino)-N-methyl-5-nitro-N-phenyl-benzamide;

5-Chloro-N-cyclopropyl-2-(4-iodo-2-methyl-phenylamino)-benzamide;

5-Fluoro-2-(4-iodo-2-methyl-phenylamino)-N-methyl-N-phenyl-benzamide;

N-Allyl-5-fluoro-2-(4-iodo-2-methyl-phenylamino)-benzamide;

N-Benzyloxy-5-iodo-2-(4-iodo-2-methyl-phenylamino)-benzamide;

5-Fluoro-2-(4-iodo-2-methyl-phenylamino)-N-(4-sulfamoyl-benzyl)-benzamide;

N-Allyl-5-chloro-2-(4-iodo-2-methyl-phenylamino)-benzamide;

N-Cyclopropyl-2-(4-iodo-2-methyl-phenylamino)-5-nitro-benzamide;

5-Bromo-N-cyclopropyl-2-(4-iodo-2-methyl-phenylamino)-benzamide;

5-Chloro-2-(4-iodo-2-methyl-phenylamino)-N-methyl-N-phenyl-benzamide;

5-iodo-2-(4-iodo-2-methyl-phenylamino)-N-(4sulfamoyl-benzyl)-benzamide;

5-Bromo-2-(4-iodo-2-methyl-phenylamino)-N-(4-sulfamoyl-benzyl)-benzamide;

N-Allyl-2-4-iodo-2-methyl-phenylamino)-5-nitro-benzamide;

2-(4-Iodo-2-methyl-phenylamino)-5-nitro-N-(4-sulfamoyl-benzyl)-benzamide;

N-Allyl-5-bromo-2-(4-iodo-2-methyl-phenylamino)-benzaide;

5-Fluoro-2-(4-iodo-2-methyl-phenylamino)-N-(3-methyl-benzyl)-benzamide;

N-Cyclopropyl-5-iodo-2-(4-iodo-2-methyl-phenylamino)-benzamide;

5-Bromo-2-(4-iodo-2-methyl-phenylamino)-N-methyl-N-phenyl-benzamide;

N-Benzyloxy-2-(4-iodo-2-methyl-phenylamino)-5-nitro-benzamide;

N-Cyclohexyl-5-iodo-2-(4iodo-2-methyl-phenylamino)-benzamide;

N-Allyl-5-iodo-2-(4-iodo-2-methyl-phenylamino)-benzamide;

5-Iodo-2-(4-iodo-2-methyl-phenylamino)-N-(3-methyl-benzyl)-benzamide;

2-(4-Iodo-2-methyl-phenylamino)-N-(3-methyl-benzyl)-5-nitro-benzamide;

5-Iodo-2-(4-iodo-2-methyl-phenylanino)-N-methyl-N-phenyl-benzamide;

N-Cyclohexyl-5-fluoro-2-(4-iodo-2-methyl-phenylamino)-benzamide;

5-Chloro-N-cyclohexyl-2-(4-iodo-2-methyl-phenylamino)-benzamide;

5-Bromo-2-(4-iodo-2-methyl-phenylamino)-N-(3-methyl-benzyl)-benzamide;

5-Bromo-N-cyclohexyl-2-(4-iodo-2-methyl-phenylamino)-benzamide;

5-Chloro-2-(4-iodo-2-methyl-phenylamino)-N-(3-methyl-benzyl)-benzamide;

N-Cyclohexyl-2-(4-iodo-2-methyl-phenylamino)-5-nitro-benzamide;

N-Benzyloxy-5-bromo-2-(4-iodo-2-methyl-phenylamino)-benzamide;

N-Benzyloxy-5-fluoro-2-(4-iodo2-methyl-phenylamino)-benzamide;

5-Chloro-N-(2-hydroxy-ethyl)-2-(4-iodo-2-methyl-phenylamino)-benzamide;

5-Bromo-N-(2-hydroxy-ethyl)-2-(4-iodo-2-methyl-phenylamino)-benzamide;

2-(4-Iodo-2-methyl-phenylamino)-N-methyl-5-nitro-N-phenyl-benzamide;

5-Chloro-2-(4-iodo-2-methyl-phenylamino)-N-methyl-N-phenyl-benzamide;

N-(2-Hydroxy-ethyl)-5-iodo-2-(4-iodo-2-methyl-phenylamino)-benzamide;

5-Chloro-N-cyclopropyl-2-(4-iodo-2-methyl-phenylamino)-benzamide;

N-Allyl-5-chloro-2-(4-iodo-2-methyl-phenylamino)-benzamide;

5-Fluoro-2-(4-iodo-2-methyl-phenylamino)-N-methyl-N-phenyl-benzamide;

N-(2-Hydroxy-ethyl)-2-(4-iodo-2-methyl-phenylamino)-5-nitro-benzamide;

5-Fluoro-N-(2-hydroxy-ethyl)-2-(4-iodo-2-methyl-phenylamino)-benzamide;

5-Bromo-N-cyclopropyl-2-(4-iodo-2-methyl-phenylamino)-benzamide;

N-Cyclopropyl-5-fluoro-2-(4-iodo-2-methyl-phenylamino)-benzamide;

5-Fluoro-2-4-iodo-2-methyl-phenylamino)-N-(4-sulfamoyl-benzyl)benzamide;

N-Cyclopropyl-2-(4-iodo-2-methyl-phenylamino)-5-nitro-benzamide;

N-Allyl-5-fluoro-2-(4-iodo-2-methyl-phenylamino)-benzamide;

N-Benzyloxy-5-iodo-2-(4iodo-2-methyl-phenylamino)-benzamide;
N-Allyl-5-bromo-2-(4-iodo-2-methyl-phenylamino)-benzamide;
5-Bromo-2-(4-iodo-2-methyl-phenylamino)-N-(4-sulfamoyl-benzyl)-benzamide;
5-Bromo-2-(4-iodo-2-methyl-phenylamino)-N-methyl-N-phenyl-benzamide;
N-Allyl-2-(4-iodo-2-methyl-phenylamino)-5-nitro-benzamide;
4-Fluoro-2-(4-iodo-2-methyl-phenylamino)-benzyl alcohol;
[5-Chloro-2-(4-iodo-2-methyl-phenylamino)-phenyl]-methanol;
[2-(4-Iodo-2-methyl-phenylamino)-5-nitro-phenyl]-methanol;
[5-Bromo-24-iodo-2-methyl-phenylamino)-phenyl]-methanol; or
N-Allyl-2-(4-iodo-2-methyl-phenylamino)-5-nitro-benzamide.

8. The method of claim 1 wherein the MEK inhibitor is a compound of Formula II

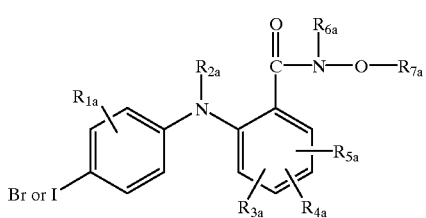

wherein:
$R_{1a}$ is hydrogen, hydroxy, $C_1$–$C_8$ alkyl, $C_1$–$C_8$ alkoxy, halo, trifluoromethyl, or CN;
$R_{2a}$ is hydrogen;
$R_{3a}$, $R_{4a}$, and $R_{5a}$ independently are hydrogen, hydroxy, halo, trifluoromethyl, $C_1$–$C_8$ alkyl, $C_1$–$C_8$ alkoxy, nitro, CN, or (O or NH)$_m$—(CH$_2$)$_n$—$R_{9a}$, where $R_{9a}$ is hydrogen, hydroxy, CO$_2$H or $NR_{10a}R_{11a}$.
n is 0–4;
m is 0 or 1;
$R_{10a}$ and $R_{11a}$ independently are hydrogen or $C_1$–$C_8$ alkyl, or taken together with the nitrogen to which they are attached can complete a 3- to 10-member cyclic ring optionally containing one, two, or three additional heteroatoms selected from O, S, NH, or N—$C_1$–$C_8$ alkyl;
$R_{6a}$ is hydrogen, $C_1$–$C_8$ alkyl,

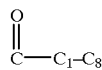

alkyl, aryl, aralkyl, or $C_3$–$C_{10}$ cycloalkyl;
$R_{7a}$ is hydrogen, $C_1$–$C_8$ alkyl, $C_2$–$C_8$ alkenyl, $C_2$–$C_8$ alkynyl, $C_3$–$C_{10}$ (cycloalkyl or cycloalkyl optionally containing a heteroatom selected from O, S, or $NR_{9a}$);
and wherein any of the foregoing alkyl, alkenyl, and alkynyl groups can be unsubstituted or substituted by cycloalkyl, aryl, aryloxy, heteroaryl, or heteroaryloxy; or $R_{6a}$ and $R_{7a}$ taken together with the N to which they are attached can complete a 5- to 10-membered cyclic ring, optionally containing one, two, or three additional heteroatoms selected from O, S, or $NR_{10a}R_{11a}$, and the pharmaceutically acceptable salts, esters, amides or prodrugs thereof.

9. The method of claim 1 wherein the MEK inhibitor is
4-Fluoro-N-hydroxy-2-(4iodo-2-methyl-phenylamino)-benzamide;
4-Fluoro-2-(4-iodo-2-methyl-phenylamino)-N-(methoxy)-benzamide;
4-Fluoro-2-(4-iodo-2-methyl-phenylamino)-N-(prop-2-ynyloxy)-benzamide;
4-Fluoro-2-(4iodo-2-methyl-phenylamino)-N-(2-phenoxyethoxy)-benzamide;
4-Fluoro-2-(4-iodo-2-methyl-phenylamino)-N-(2-thienylmethoxy)-benzamide;
4-Fluoro-2-(4-iodo-2-methyl-phenylamino)-N-(prop-2-enyloxy)-benzamide;
4-Fluoro-2-(4-iodo-2-methyl-phenylamino)-N-(cyclopropylmethoxy)-benzamide;
4-Fluoro-2-(4iodo-2-methyl-phenylamino)-N-(cyclopentoxy)-benzamide;
3,4-Difluoro-2-(4-iodo-2-methyl-phenylamino)-N-(3-furylmethoxy)-benzamide;
3,4-Difluoro-2-(4-iodo-2-methyl-phenylamino)-N-ethoxy-benzamide;
3,4-Difluoro-2-(4-iodo-2-methyl-phenylamino)-N-(but-2-enyloxy)-benzamide;
3,4-Difluoro-2-(4-iodo-2-methyl-phenylamino)-N-(cyclopropyl-methoxy)-benzamide;
3,4-Difluoro-2-(4-iodo-2-methyl-phenylamino)-N-(1-methylprop-2-ynyloxy)-benzamide;
3,4-Difluoro-2-(4-iodo-2-methyl-phenylamino)-N-(3-phenylprop-2-ynyloxy)-benzamide;
3,4-Difluoro-2-(4-iodo-2-methyl-phenylamino)-N-(3-methyl-5-phenylpent-2-en4-ynyloxy)-benzamide;
3,4-Difluoro-2-(4-iodo-2-methyl-phenylamino)-N-(prop-2-ynyloxy)-benzamide;
3,4-Difluoro-2-(4iodo-2-methyl-phenylamino)-N-(propoxy)-benzamide;
3,4-Difluoro-2-(4-iodo-2-methyl-phenylamino)-N-(cyclobutyloxy)-benzamide;
3,4-Difluoro-2-(4-iodo-2-methyl-phenylamino)-N-(2-thienylmethoxy)-benzamide;
3,4-Difluoro-2-(4-iodo-2-methyl-phenylamino)-N-(2-methyl-prop-2-enyloxy)-benzamide;
3,4-Difluoro-2-(4-iodo-2-methyl-phenylamino)-N-(2-phenoxyethoxy)-benzamide;
3,4-Difluoro-2-(4-iodo-2-methyl-phenylamino)-N-(but-2-enyloxy)-benzamide;
3,4-Difluoro-2-(4-iodo-2-methyl-phenylamino)-N-(but-3-ynyloxy)-benzamide;
3,4-Difluoro-2-(4-iodo-2-methyl-phenylamino)-N-(cyclopentyloxy)-benzamide;
3,4-Difluoro-2-(4-iodo-2-methyl-phenylamino)-N-(3-(2-fluorophenyl)-prop-2-ynyloxy)-benzamide;
5-Bromo-3,4-ifluoro-N-hydroxy-2-(4-iodo-2-methyl-phenylamino)-benzamide;
5-Bromo-3,4difluoro-2-(4-iodo-2-methyl-phenylamino)-N-(n-propoxy)-benzamide;
5-Bromo-3,4-difluoro-N-(firan-3-ylmethoxy)-2-(4-iodo-2-methyl-phenylamino)-benzamide;

5-Bromo-N-(but-2-enyloxy)-3,4-difluoro-2-(4-iodo-2-methyl-phenylamino)-benzamide 5-Bromo-N-butoxy-3,4-difluoro-2-(4-iodo-2-methyl-phenylamino)-benzamide;

5-Bromo-3,4-difluoro-2-(4-iodo-2-methyl-phenylamino)-N-(3-methyl-but-2-enyloxy)-benzamide;

5-Bromo-3,4difluoro-2-(4-iodo-2-methyl-phenylamino)-N-(3-methyl-pent-2-en4ynyloxy)-benzamide;

5-Bromo-3,4-difluoro-2-(4-iodo-2-methyl-benzyl)-N-[5-(3-methoxy-phenyl)-3-methyl-pent-2-en4-ynyloxy]-benzamide;

5-Bromo-3,4-difluoro-2-(4-iodo-2-methyl-phenylamino)-N-(prop-2-ynyloxy)-benzamide;

5-Bromo-3,4-difluoro-2-(4-iodo2-methyl-phenylamino)-N-[3-(3-methoxy-phenyl)-prop-2-ynyloxy]-benzamide;

5-Bromo-3,4-difluoro-2-(4-iodo-2-methyl-phenylamino)-N-(thiopen-2-ylmethoxy)-benzamide;

5-Bromo-3,4-difluoro-2-4-iodo-2-methyl-phenylamino)-N-(pyridin-3-ylmethoxy)-benzamide;

5-Bromo-3-4difluoro-2-(4-iodo-2-methyl-phenylamino)-N-(3-(2-fluorophenyl)-prop-2-ynyloxy)-benzamide;

5-Bromo-3,4-difluoro-2-(4-iodo-2-methyl-phenylamino)-N-(ethoxy)-benzamide;

5-Bromo-3,4-difluoro-2-(4-iodo-2-methyl-phenylamino)-N-(cyclopropylmethoxy)-benzamide;

5-Bromo-3,4-difluoro-2-(4-iodo-2-methyl-phenylamino)-N-(isopropoxy)-benzamide;

5-Bromo-3,4-difluoro-2-(4-iodo-2-methyl-phenylamino)-N-but-3-ynyloxy)-benzamide;

5-Chloro-N-hydroxy-2-4-iodo-2-methyl-phenylamino)-benzamide;

5-Chloro-2)4-iodo-2-methyl-phenylamino)-N-(tetrahydro-pyran-2-yloxy)-benzamide;

5-Chloro-2-(4-iodo2-methyl-phenylamino)-N-methoxy-benzamide;

4-Bromo-2-(4-iodo-2-methyl-phenylamino)-N-phenylmethoxy-benzamide;

4-Fluoro-2-(4-iodo-2-methyl-phenylamino)-N-phenylmethoxy-benzamide;

5-Fluoro-N-hydroxy-2-(4-iodo-2-methyl-phenylamino)-benzamide;

5-Iodo-2-(4-iodo-2-methyl-phenylamino)-N-phenylmethoxy-benzamide;

5-Fluoro-2-(4-iodo-2-methyl-phenylamino)-N-(tetrahydropyran-2-yloxy)-benzamide;

3,4-Difluoro-2-(4-bromo-2-methyl-phenylamino)-N-(3-phenylprop-2-ynyloxy)-benzamide;

3,4-Difluoro-2-(4bromo-2-methyl-phenylamino)-N-(3-furylmethoxy)-benzamide;

3,4-Difluoro-2-(4-bromo-2-methyl-phenylamino)-N-(2-thienylmethoxy)-benzamide;

3,4Difluoro-2-(4-bromo-2-methyl-phenylamino)-N-(but-3-ynyloxy)-benzamide;

3,4-Difluoro-2-(4-bromo-2-methyl-phenylamino)-N-(2-methyl-prop-2-enyloxy)-benzamide;

3,4-Difluoro-2-(4-bromo-2-methyl-phenylamino)-N-(but-2-enyloxy)-benzamide;

3,4-Difluoro-2-(4-bromo-2-methyl-phenylamino)-N-(methoxy)-benzamide;

3,4-Difluoro-2-(4-bromo-2-methyl-phenylamino)-N-(ethoxy)-benzamide;

3,4-Difluoro-2-(4-bromo-2-methyl-phenylamino)-N-(cyclobutoxy)-benzamide;

3,4-Difluoro-2-(4-bromo-2-methyl-phenylamino)-N-(isopropoxy)-benzamnide;

3,4-Difluoro-2-(4-bromo-2-methyl-phenylamino)-N-(2-phenoxyethoxy)-benzamide;

3,4-Difluoro-2-(4-bromo-2-methyl-phenylamino)-N-(cyclopropyl-methoxy)-benzamide;

3,4-Difluoro-2-(4-broino-2-methyl-phenylamino)-N-(n-propoxy)-benzamide;

3,4-Difluoro-2-(4-bromo-2-methyl-phenylamino)-N-(1-methyl-prop-2-ynyloxy)-benzamide;

3,4-Difluoro-2-(4-bromo-2-methyl-phenylamino)-N-(3-(3-fluorophenyl)-prop-2-ynyloxy)-benzamide;

3,4-Difluoro-2-(4-bromo-2-methyl-phenylamino)-N-(4,4-dimethylpent-2-ynyloxy)-benzamide;

3,4-Difluoro-2-(4-bromo-2-methyl-phenylamino)-N-(cyclopentoxy)-benzamide;

3,4,5-Trifluoro-N-hydroxy-2-(4-iodo-2-methyl-phenylamino)-benzamide;

5-Chloro-3,4-difluoro-N-hydroxy-2-(4-iodo-2-methyl-phenylamino)-benzamide;

5-Bromo-3,4difluoro-2-(2-fluoro-4-iodo-phenylamiino)-N-hydroxy-benzamide;

N-Hydroxy-2-(4-iodo-2-methyl-phenylamino)-4-nitro-benzamide;

3,4,5-Trifluoro-2-(2-fluoro4-iodo-phenylamino)-N-hydroxy-benzamide;

5-Chloro-3,4-difluoro-2-(2-fluoro-4-iodo-phenylamino)-N-hydroxy-benzamide;

5-Bromo-2-(2-chloro-4-iodo-phenylamino)-3,4-difluoro-N-hydroxy-benzamide;

2-(2-Fluoro[]iodo-phenylamino)-N-hydroxy-4-nitro-benzamide;

2-(2-Chloro4-iodo-phenylamino)-3,4,5-trifluoro-N-hydroxy-benzamide;

5-Chloro-2-(2-chloro-4-iodo-phenylamino)-3,4-difluoro-N-hydroxy-benzamide;

5-Bromo-2-(2-bromo-4-iodo-phenylamino)-3,4-difluoro-N-hydroxy-benzamide;

2-(2-Chloro-4iodo-phenylamino)-N-hydroxy-4-methyl-benzamide;

2-(2-Bromo4-iodo-phenylamino)-3,4,5-trifluoro-N-hydroxy-benzamide;

2-(2-Bromo-4-iodo-phenylamino)-5-chloro-3,4-difluoro-N-hydroxy-benzamide;

2-(2-Bromo4-iodo-phenylamino)-N-hydroxy4-nitro-benzamide;

4-Fluoro-2-(2-fluoro-4-iodo-phenylamino)-N-hydroxy-benzamide;

3,4-Difluoro-2-2-fluoro[]4iodo-phenylamino)-N-hydroxy-benzamide;

2-(2-Choro-4-iodo-phenylamino)4-fluoro-N-hydroxy-benzamide;

2-(2-Chloro4-iodo-phenylamino)-3,4-fluoro-N-hydroxy-benzamide;

2-(2-Bromo-4-iodo-phenylamino)4-fluoro-N-hydroxy-benzamide;

2-(2-Bromo4-iodo-phenylamino)-3,4-fluoro-N-hydroxy-benzamide;

N-Cyclopropylmethoxy-3,4,5-trifluoro-2-(4-iodo-2-methyl-phenylamino)-benzamide;

5-Chloro-N-cyclopropylmethoxy-3,4-difluoro-2-(4-iodo-2-methyl-phenylamnino-benzamide;

5-Bromo-N-cyclopropyhnethoxy-3,4-difluoro-2-(2-fluoro-4-iodo-phenylamino)-benzamide;

N-Cyclopropylmethoxy-2-(4iodo-2-methyl-phenylamino)-4-nitro-benzamide;

N-Cyclopropylmethoxy-3,4,5-trifluoro-2-(2-fluoro-4-iodo-phenylamino)-benzamide;

5-Chloro-N-cyclopropylmethoxy-3,4-difluoro-2-(2-fluoro4-iodo-phenylamino)-benzamide;

5-Bromo-2-(2-chloro-4-iodo-phenylamino)-N-cyclopropylmethoxy-3,4-difluoro-benzamide;

N-Cyclopropylmethoxy-2-(2-fluoro-4-iodo-phenylamino)-4-nitro-benzamide;

2-(2-Chloro-4-iodo-phenylamino)-N-cyclopropylmethoxy-3,4,5-trifluoro-benzamide;

5-Chloro-2-(2-chloro-4-iodo-phenylamino)-N-cyclopropylmethoxy-3,4-difluoro-benzamide;

5-Bromo-2-(2-bromo4iodo-phenylamino)-N-ethoxy-3,4-difluoro-benzamide;

2-(2-Chloro-4-iodo-phenylamino)-N-ethoxy-4-nitro-benzamide;

2-(2-Bromo4-iodo-phenylamino)-N-cyclopropylmethoxy-3,4,5-trifluoro-benzamide;

2-(2-Bromo-4-iodo-phenylamino)-5-chloro-N-cyclopropylmethoxy-3,4-difluoro-benzamide 2-(2-Bromo4-iodo-phenylamino)-N-cyclopropylmethoxy4-nitro-benzamide;

N-Cyclopropylmethoxy4-fluoro-2-(2-fluoro4-iodo-phenylamino)-benzamide;

N-Cyclopropylmethoxy-3,4-difluoro-2-(2-fluoro4iodo-phenylamino)-benzamide;

2-(2-Chloro-4-iodo-phenylamino)-N-cyclopropylmethoxy-4-fluoro-benzamide;

2-(2-Chloro4-iodo-phenylamino)-N-cyclopropylmethoxy-3,4-difluoro-benzamide;

2-(2-Bromo4-iodo-phenylamino)-N-cyclopropylmethoxy4-fluoro-benzamide; or 2-(2-Bromo-4iodo-phenylamino)-N-cyclopropylmethoxy-3,4difluoro-benzamide.

* * * * *